United States Patent
Ashok et al.

(10) Patent No.: US 11,669,968 B2
(45) Date of Patent: Jun. 6, 2023

(54) OPHTHALMIC DEVICE

(71) Applicant: Optos PLC, Dunfermline Fife (GB)

(72) Inventors: Praveen Ashok, Scotland (GB); Alan Anderson, Scotland (GB); Gonzalo Muyo, Scotland (GB); Alistair Gorman, Scotland (GB); Jano Van Hemert, Scotland (GB)

(73) Assignee: Optos Plc, Dunfermline (GB)

( * ) Notice: Subject to any disclaimer, the term of this patent is extended or adjusted under 35 U.S.C. 154(b) by 471 days.

(21) Appl. No.: 16/637,023

(22) PCT Filed: Aug. 14, 2017

(86) PCT No.: PCT/EP2017/070579
§ 371 (c)(1),
(2) Date: Feb. 6, 2020

(87) PCT Pub. No.: WO2019/034230
PCT Pub. Date: Feb. 21, 2019

(65) Prior Publication Data
US 2020/0242768 A1  Jul. 30, 2020

(51) Int. Cl.
*G06K 9/00* (2022.01)
*G06T 7/00* (2017.01)
(Continued)

(52) U.S. Cl.
CPC .......... *G06T 7/0014* (2013.01); *A61B 3/0008* (2013.01); *A61B 3/0025* (2013.01);
(Continued)

(58) Field of Classification Search
None
See application file for complete search history.

(56) References Cited

U.S. PATENT DOCUMENTS

| | | | |
|---|---|---|---|
| 5,815,242 A | 9/1998 | Anderson |
| 7,959,290 B2 | 6/2011 | Cairns |
| 8,970,847 B2 | 3/2015 | Ono |
| 10,535,958 B2 | 1/2020 | Kondo |

(Continued)

FOREIGN PATENT DOCUMENTS

| | | |
|---|---|---|
| CN | 103251381 A | 6/2013 |
| CN | 105934193 A | 9/2016 |

(Continued)

OTHER PUBLICATIONS

International Search Report (dated Apr. 30, 2018) issued in international application No. PCT/EP2017/070579.

(Continued)

*Primary Examiner* — Wei Wen Yang
(74) *Attorney, Agent, or Firm* — DeLucia, Mlynar & Associates LLP

(57) ABSTRACT

A method of controlling an ophthalmic device operable to image an imaging region of a retina and concurrently illuminate an illumination region of the retina, the method including acquiring a reference retinal image by imaging a reference imaging area of the retina; designating a target in the reference retinal image; acquiring a current retinal image of an initial imaging region within the reference imaging area; moving the imaging region from the initial imaging region to a destination imaging region using the target and the reference retinal image, and acquiring a retinal image of the destination imaging region; illuminating the illumination region while the imaging region is the destination imaging region; acquiring one or more retinal images while the illumination module is being illuminated; and comparing a marker retinal image based on the one or more retinal image(s) with a comparison image based on the reference retinal image.

21 Claims, 14 Drawing Sheets

(51) Int. Cl.
*A61B 3/00* (2006.01)
*A61B 3/10* (2006.01)
*A61B 3/12* (2006.01)

(52) U.S. Cl.
CPC ............ *A61B 3/102* (2013.01); *A61B 3/1025* (2013.01); *A61B 3/12* (2013.01); *G06T 2207/30041* (2013.01); *G06T 2207/30204* (2013.01)

(56) References Cited

U.S. PATENT DOCUMENTS

| | | |
|---|---|---|
| 2010/0141895 A1 | 6/2010 | Cairns |
| 2010/0149489 A1 | 6/2010 | Kikawa et al. |
| 2012/0165799 A1* | 6/2012 | Yamamoto .......... A61F 9/00821 606/4 |
| 2013/0215384 A1 | 8/2013 | Hirose |
| 2016/0000324 A1* | 1/2016 | Rege .................... A61B 3/1208 600/479 |
| 2016/0295109 A1 | 10/2016 | Henriksen |
| 2018/0116501 A1* | 5/2018 | Akiba .................... G01N 21/17 |
| 2020/0196863 A1* | 6/2020 | Anderson ............ A61B 3/0008 |

FOREIGN PATENT DOCUMENTS

| | | |
|---|---|---|
| EP | 21476334 A1 | 1/2020 |
| JP | 3490088 B2 | 1/2004 |
| JP | 2006289579 A1 | 12/2008 |
| JP | 2 147 634 A1 | 1/2010 |
| JP | 2010 012109 A | 1/2010 |
| JP | 2012-135550 A | 7/2012 |
| JP | 2 497 414 A1 | 9/2012 |
| JP | 2012-196439 A | 10/2012 |
| JP | 5330236 B2 | 10/2013 |
| JP | 2017 127580 A | 7/2017 |
| WO | WO95/13012 A2 | 5/1995 |
| WO | WO2008/009877 A1 | 1/2008 |

OTHER PUBLICATIONS

Written opinion (dated Apr. 30, 2018) of the international Searching Authority issued in international application No. PCT/EP2017/070579.
U.S. Appl. No. 16/636,999, filed Feb. 6, 2020.
U.S. Appl. No. 16/637,052, filed Feb. 6, 2020.
U.S. Appl. No. 16/637,075, filed Feb. 6, 2020.
Office Action dated Feb. 9, 2022, issued in Chinese Patent Application No. 20178095530.0 (7 Sheets) (English Summary of Office Action Rejections attached (4 Sheets)).
Decision to Grant a Patent dated Sep. 8, 2022 in Japanese patent application No. 2020-508466 (1 sheet). (English translation attached: 2 sheets).

* cited by examiner

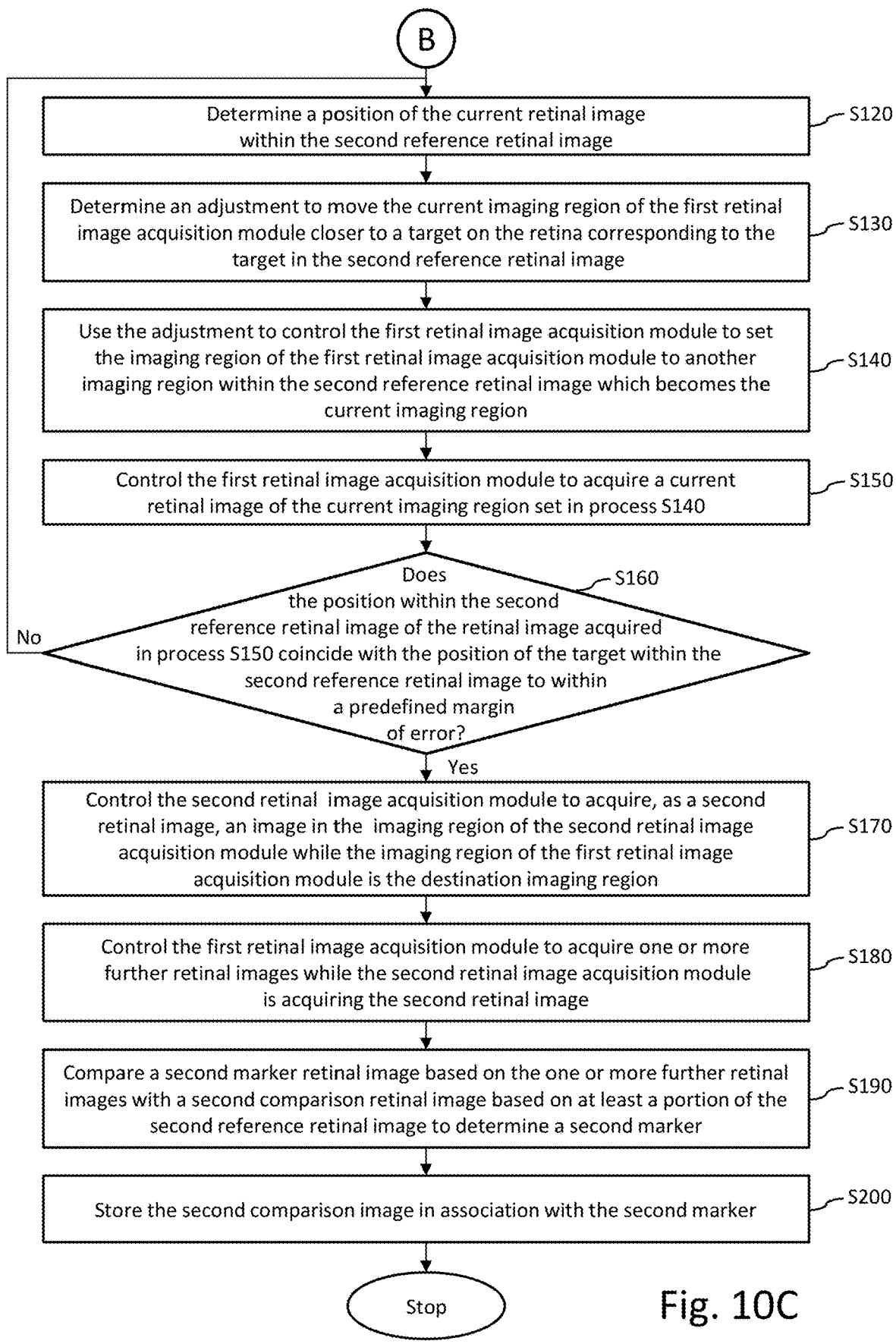

OPHTHALMIC DEVICE

This application is a national phase filing under 37 U.S.C. § 371 based on International Application No. PCT/EP2017/070579, filed Aug. 14, 2017, and claims the benefit of priority of that International Application. The contents of the International Application are incorporated by reference herein.

TECHNICAL FIELD

The present invention generally relates to the field of ophthalmic devices and, more particularly, to ophthalmic devices having an imaging module for imaging the retina of an eye.

BACKGROUND

To increase the amount of information extracted during a visual examination of the retina of a subject's eye, some known ophthalmic devices combine two or more different kinds of retinal image acquisition module to simultaneously acquire retinal images of different modality during the examination, which can yield complementary information that may be valuable for diagnostic purposes. For example, some known ophthalmic devices combine scanning laser ophthalmoscope (SLO) functionality with optical coherence tomography (OCT) functionality to acquire two-dimensional SLO images of the retinal surface and tomographic images for generating a three-dimensional image of the retina beneath the same part of the retinal surface. These kinds of ophthalmic devices can generally operate in the SLO and OCT imaging modes individually, or in combination, in accordance with user requirements.

More generally, ophthalmic devices having a retinal image acquisition module with a relatively short scan time, and an illumination module with a longer scan time for illuminating with a light beam (and optionally also imaging) a region of the retina, allow the ophthalmologist or the like to use the retinal image acquisition module to acquire a reference image of the retina and identify therein a region of interest for further examination and/or treatment using the light beam. Treatment (or imaging, as the case may be) of the region of interest can then be performed using the illumination module, with device calibration data being employed to convert points in the reference image demarcating the region of interest to device settings for guiding the illumination module to the corresponding region of the retina.

SUMMARY

In the known kinds of ophthalmic device discussed above, however, it can be difficult to reliably establish a positional relationship between the scans performed by the retinal imaging module and the illumination module owing to eye movements and systematic errors, for example, and this can adversely affect the effectiveness of the treatment applied or the usefulness of the complementary information acquired in the different modalities (as the case may be).

The present inventors have devised a method of controlling an ophthalmic device having a first retinal image acquisition module operable to image an imaging region of a retina and an illumination module operable to concurrently illuminate an illumination region of the retina, the imaging region and the illumination region having a predetermined positional relationship to one another, the method comprises: controlling the first retinal image acquisition module to acquire a reference retinal image by imaging a reference imaging area of the retina; designating a target in the reference retinal image; controlling the first retinal image acquisition module to acquire a current retinal image of an initial imaging region within the reference imaging area; controlling the first retinal image acquisition module to move its imaging region of the retina from the initial imaging region to a destination imaging region using the target and at least a portion of the reference retinal image, and to acquire a retinal image of the destination imaging region; controlling the illumination module to illuminate the illumination region of the retina while the imaging region of the first retinal image acquisition module is the destination imaging region; controlling the first retinal image acquisition module to acquire one or more retinal images while the illumination module is illuminating the illumination region of the retina; and comparing a marker retinal image based on the one or more retinal images with a comparison image based on at least a portion of the reference retinal image to determine a marker that is indicative of the position of the marker retinal image within the comparison image.

The inventors have further devised a computer-readable storage medium and a signal carrying storing computer program instructions which, when executed by a processor, cause the processor to perform a method as set out above.

The inventors have further devised a controller for controlling an ophthalmic device having a first retinal image acquisition module operable to image an imaging region of a retina and an illumination module operable to concurrently illuminate an illumination region of the retina, the imaging region and the illumination region having a predetermined positional relationship to one another. The controller comprises a processor and a memory storing computer program instructions which, when executed by the processor, cause the processor to perform a method as set out above.

The inventors have further devised an ophthalmic device comprising a retinal image acquisition module arranged to acquire a retinal image of an imaging area of the retina of an eye, and an illumination module operable to concurrently illuminate an illumination region of the retina, the imaging region and the illumination region having a predetermined positional relationship to one another. The ophthalmic device further comprises a controller as set out above, which is arranged to control the retinal image acquisition module and the illumination module.

BRIEF DESCRIPTION OF THE DRAWINGS

Embodiments of the invention will now be explained in detail, by way of non-limiting example only, with reference to the accompanying figures, in which:

FIGS. 10A to 10C are flow diagrams illustrating processes by which the controller of the embodiment may control the ophthalmic device to acquire a first 3D image of a region of the retina in an initial scan of the subject's eye, and a second 3D image of the region in a repeat scan of the subject's eye;

DETAILED DESCRIPTION OF EMBODIMENTS

Embodiments of the present invention will now be described in detail with reference to the accompanying drawings.

Figure 1A:
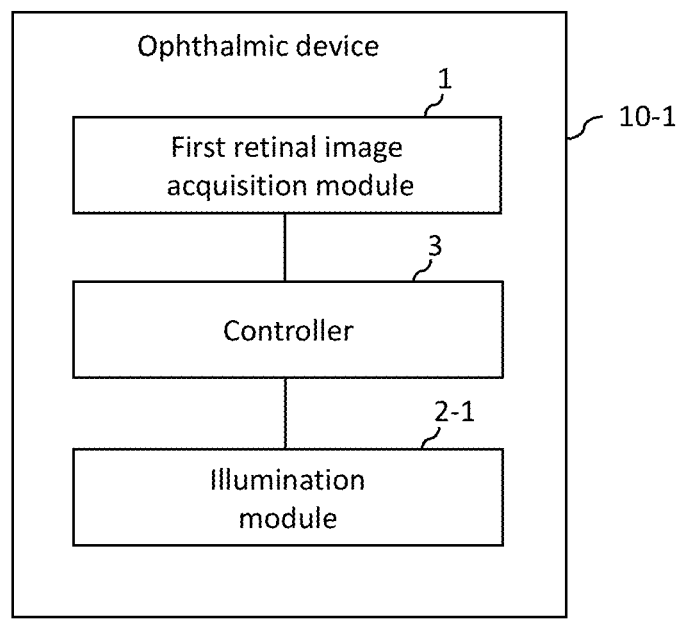
FIGS. 1A and 1B are a block diagrams illustrating components of an ophthalmic device according to embodiments of the present invention.

FIG. 1A is a schematic illustration of an ophthalmic device 10-1 comprising a first retinal image acquisition module 1, which is arranged to image an imaging region of the retina of an eye of a subject (not shown in FIG. 1A). The ophthalmic device 10-1 also includes an illumination module 2-1 which is operable to concurrently (i.e. while the first retinal image acquisition module 1 is imaging the imaging region of the retina) illuminate an illumination region the retina. The illumination module 2-1 may take the form of a laser configured to emit a light beam whose characteristics (such as wavelength and intensity) are suitable for treating the retina, for example. The illumination module 2-1 may, however, be configured to not only illuminate a region of the retina but also receive and process light reflected from the illuminated region so as to acquire an image of the region; the illumination module 2-1 may thus comprise a second retinal image acquisition module (as shown at 2-2 in the ophthalmic device 10-2 illustrated in FIG. 1B) which is different from the first retinal image acquisition module 1, and which may have a retinal image acquisition time that is longer than that of the first retinal image acquisition module 1.

Figure 1B:
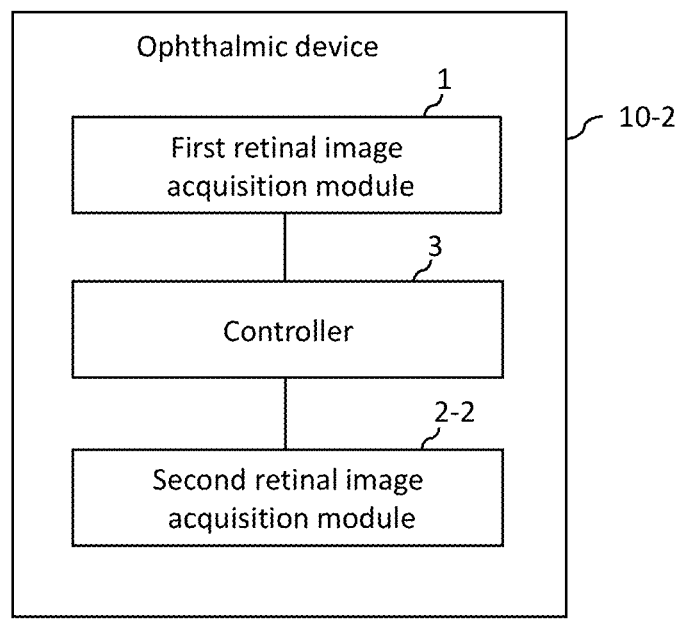

The first and second retinal image acquisition modules 1 and 2-2 may, as in the embodiment of FIG. 1B, be operable in a combined imaging mode to transmit and receive light along a common optical path so as to concurrently image substantially the same region of the retina. The first and second retinal image acquisition modules 1 and 2-2 may, however, be operable in the combined imaging mode to transmit and receive light along respective optical paths having a fixed positional relationship to one another, so as to concurrently image respective regions of the retina that are different from one another. The second retinal image acquisition module 2-2 may thus be operable in the combined imaging mode to acquire a retinal image of a imaging region of the retina having a predetermined positional relationship to the concurrently imaged imaging region of the first retinal image acquisition module 1 for the eye under examination, and which need not be the same in size as the concurrently imaged imaging region of the first retinal image acquisition module 1. In other words, the respective imaging regions on the retina concurrently imaged by the first and second retinal image acquisition modules 1 and 2-2 may have centers (e.g. geometric centers) that are not coincident but offset from each other by a known amount in a known direction, which can be determined by calibration, for example. It should be noted that, although the ophthalmic device 10-2 of the present embodiment comprises two retinal image acquisition modules, the ophthalmic device may alternatively have only a single retinal image acquisition module, or three or more retinal image acquisition modules that are operable in a combined imaging mode to concurrently image respective imaging regions of the retina having a predetermined positional relationship to each other.

The ophthalmic devices 10-1 and 10-2 each have a controller 3, which is configured to control the first image acquisition module 1 and the illumination module 2-1 in the case of ophthalmic device 10-1 shown in FIG. 1A, and the first and second retinal image acquisition modules 1 and 2-2 in the case of ophthalmic device 10-2 shown in FIG. 1B, in the manner described below.

Figure 2:
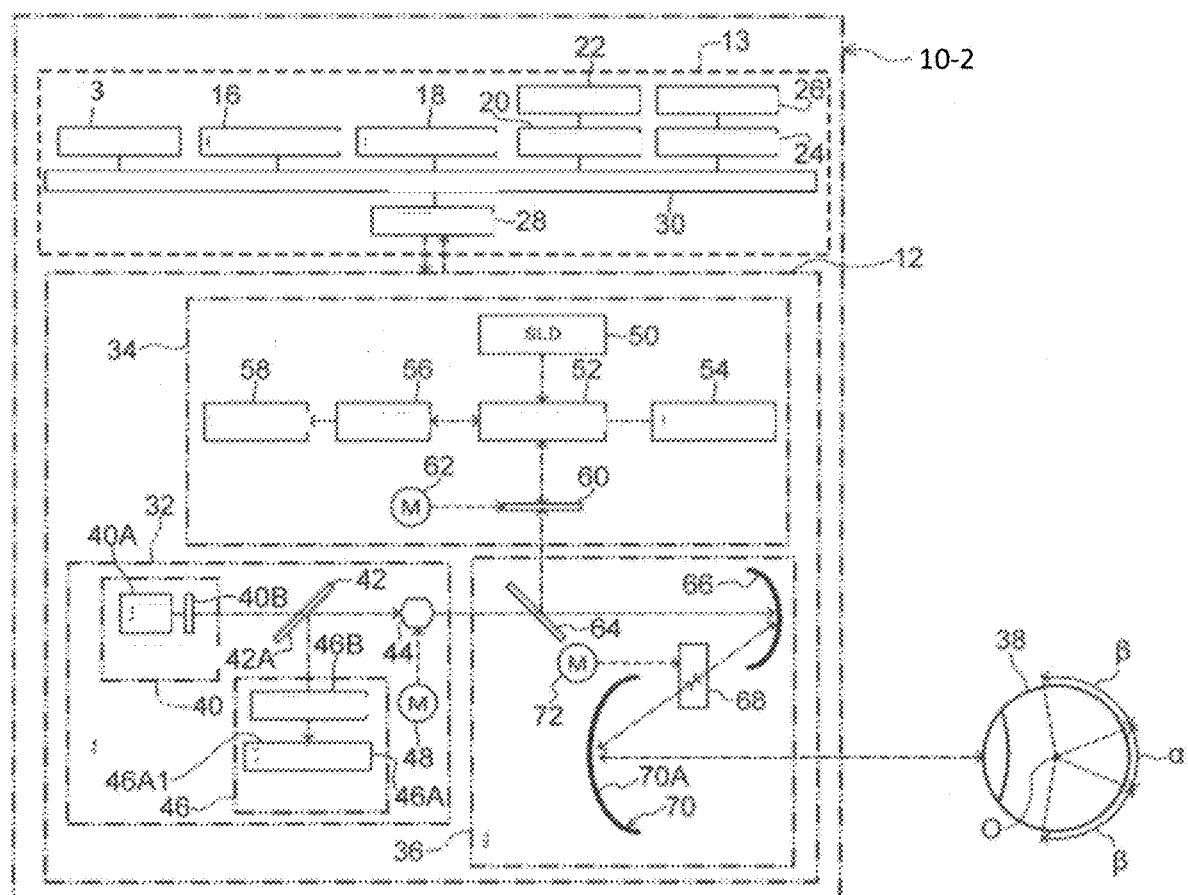
FIG. 2 is a block diagram illustrating an implementation of the ophthalmic device illustrated in FIG. 1B, in the exemplary form of a combined SLO-OCT scanner.

The ophthalmic device 10-2 may, as in the present embodiment, take the exemplary form of a combined SLO and OCT scanner, comprising a device main body 12 that includes an SLO unit 32, an OCT unit 34, and a shared optical system 36, as illustrated in FIG. 2. The ophthalmic device 10-2 also has a device main body controller 13 comprising the controller 3.

The ophthalmic device 10-2 thus includes SLO imaging system functionality, which is functionality for imaging using SLO, and OCT imaging system functionality, which is functionality for imaging using OCT. The SLO imaging system functionality is implemented by the device main body controller 13, the SLO unit 32, and the shared optical system 36. The OCT imaging system functionality is implemented by the device main body controller 13, the OCT unit 34, and the shared optical system 36. The SLO unit 32, the shared optical system 36 and the SLO image generator 18 shown in FIG. 2 together provide an example of the first retinal image acquisition module 1 of FIG. 1A, and the OCT unit 34, the shared optical system 36 and the OCT image generator 16 together provide an example of the second retinal image acquisition module 2-2. Thus, the first and second retinal imaging modules 1 and 2-2 share some optical components (namely, the shared optical system 36) in the present embodiment. The first and second retinal imaging modules 2-1 and 2-2 may, however, alternatively be provided as separate units that do not share any optical components.

The ophthalmic device 10-2 is operable in an SLO mode, which is an operation mode that exercises the SLO imaging system functionality, an OCT mode, which is an operation mode that exercises the OCT imaging system functionality, and the aforementioned combined imaging mode that exercises both the SLO imaging system functionality and the OCT imaging system functionality at the same time. These operation modes may be selectively set according to user instructions or sequence control.

The SLO unit 32 may, as in the present embodiment, include an emission section 40, a beam splitter 42, a polygon mirror 44, a photo detector section 46, and a motor 48, that are configured to generate a two-dimensional image of the retina of a subject's eye 38.

Hereafter, in a case in which, for example, the ophthalmic device 10-1 or 10-2 is installed on a horizontal surface, a direction substantially perpendicular to the horizontal surface (not illustrated in the drawings) is denoted the "Y direction" for convenience of explanation. For example, a direction that is substantially parallel to a horizontal surface and that is the depth direction of the subject's eye 38 positioned in a state in which the anterior segment is facing an eyepiece lens (not illustrated in the drawings) of the ophthalmic device 10-1 to 10-2, in a case in which the ophthalmic device 10-1 or 10-2 is installed on the horizontal surface, is denoted the "Z direction" hereafter for convenience of explanation. Hereafter, a direction substantially perpendicular to both the Y direction and the Z direction is denoted the "X direction" hereafter for convenience of explanation.

The emission section 40 includes a light source 40A and a bandpass filter 40B. The light source 40A is a light source for imaging using SLO, and may emit light having a wavelength in a range of from approximately 400 nanometers to approximately 1100 nanometers. Light emitted from the light source 40A passes through the bandpass filter 40B such that only light having specific wavelengths is emitted onto the beam splitter 42.

In the present embodiment, light emitted from the emission section 40 is broadly split into visible red and green (RG) light and near-infrared light, which is light having a wavelength in the near-infrared region of the spectrum.

In the present embodiment, RG light and near-infrared light are selectively emitted from the emission section 40 by varying the wavelength of the light produced by the light source 40A, and by applying the bandpass filter 40B to the light produced by the light source 40A.

For convenience of explanation, RG light and near-infrared light, serving as the light emitted from the emission section 40, are simply referred to as "SLO light" hereafter in a case in which explanation does not need to distinguish between the two.

The beam splitter 42 guides the SLO light to the polygon mirror 44 by transmitting the SLO light, and guides first retina reflected light to the photo detector section 46. Here, first retina reflected light denotes light reflected by the retina originating from the SLO light. Light reflected by the retina denotes light that was reflected by the retina and was then incident on the shared optical system 36.

The polygon mirror 44 sends the SLO light from the beam splitter 42 to the shared optical system 36. Then, as illustrated as an example in FIG. 3, the polygon mirror 44 scans the SLO light in the Y direction by rotating in the arrow A direction on receiving drive force of the motor 48.

The photo detector section 46 includes a photo detector 46A and an optical filter 46B. The optical filter 46B is disposed at a position between an optical reception face 46A1 of the photo detector 46A and a reflecting face 42A of the beam splitter 42, and covers an optical reception face 46A1. First retina reflected light made of near-infrared light and first retina reflected light made of RG light are selectively made incident to the optical reception face 46A1.

The photo detector 46A generates an SLO image signal, which is an image signal based on the first retina reflected light that was incident via the optical filter 46B, and outputs the generated SLO image signal.

The OCT unit 34 is employed to generate a tomographic image of the retina, and may, as in the present embodiment, include a super-luminescent diode (SLD) 50, an optical coupler 52, a reference light optical system 54, a spectrophotometer 56, a line sensor 58, a V-galvanometer mirror 60, and a motor 62.

The SLD 50 emits low-coherence light. Low-coherence light, for example, denotes light encompassing light in the near-infrared region having a longer wavelength than near-infrared light emitted from the emission section 40 and having a time-wise coherence length of approximately several tens of micrometers.

Low-coherence light emitted from the SLD 50 is fed into the optical coupler 52 via a first optical fiber (not illustrated in the drawings) and is split into reference light and signal light. The reference light is guided to the reference light optical system 54 via a second optical fiber (not illustrated in the drawings), and the signal light is guided to the V-galvanometer mirror 60 via a third optical fiber (not illustrated in the drawings).

The reference light optical system 54 is an optical delay line which matches the optical path length between the eye 38 and the optical coupler 52.

The reference mirror returns reference light to the optical coupler 52 via the same optical path by reflecting the reference light. The reference mirror is a movable mirror that can move in the direction of the optical axis of the reference light, and the length of the optical path of the reference light is adjusted by moving the position of the reference mirror on the optical axis.

The V-galvanometer mirror 60 sends signal light to the shared optical system 36. Then, as illustrated as an example in FIG. 3, the V-galvanometer mirror 60 scans the signal light in the Y direction by rotationally oscillating in the arrow B direction on receiving drive force of the motor 62.

Moreover, the V-galvanometer mirror 60 guides second retina reflected light to the optical coupler 52 via a fourth optical fiber. Here, the second retina reflected light denotes light reflected by the retina originating from signal light.

The second retina reflected light guided by the optical coupler 52 is superimposed with the reference light guided from the reference light optical system to the optical coupler 52 by the optical coupler 52 and interference occurs. Interference light obtained due to the interference occurring is spectrally dispersed by the spectrophotometer 56, and the spectrally dispersed interference light is guided to the line sensor 58.

The line sensor 58 generates an OCT image signal, which is an image signal based on incident interference light, and outputs the generated OCT image signal.

The shared optical system 36 may, as in the present embodiment, include a dichroic mirror 64, a slit mirror 66 that has an elliptical, concave reflecting face, an H-galvanometer mirror 68, an ellipsoid mirror 70, and a motor 72.

The dichroic mirror 64 guides the SLO light to the slit mirror 66 by causing the SLO light from the polygon mirror 44 of the SLO unit 32 to be transmitted, and guides the signal light to the slit mirror 66 by causing the signal light from the V-galvanometer mirror 60 of the OCT unit 34 to be reflected.

For convenience of explanation, signal light and SLO light are denoted "emitted light" hereafter in a case in which there is no need for the explanation to distinguish between the two.

Figure 3:
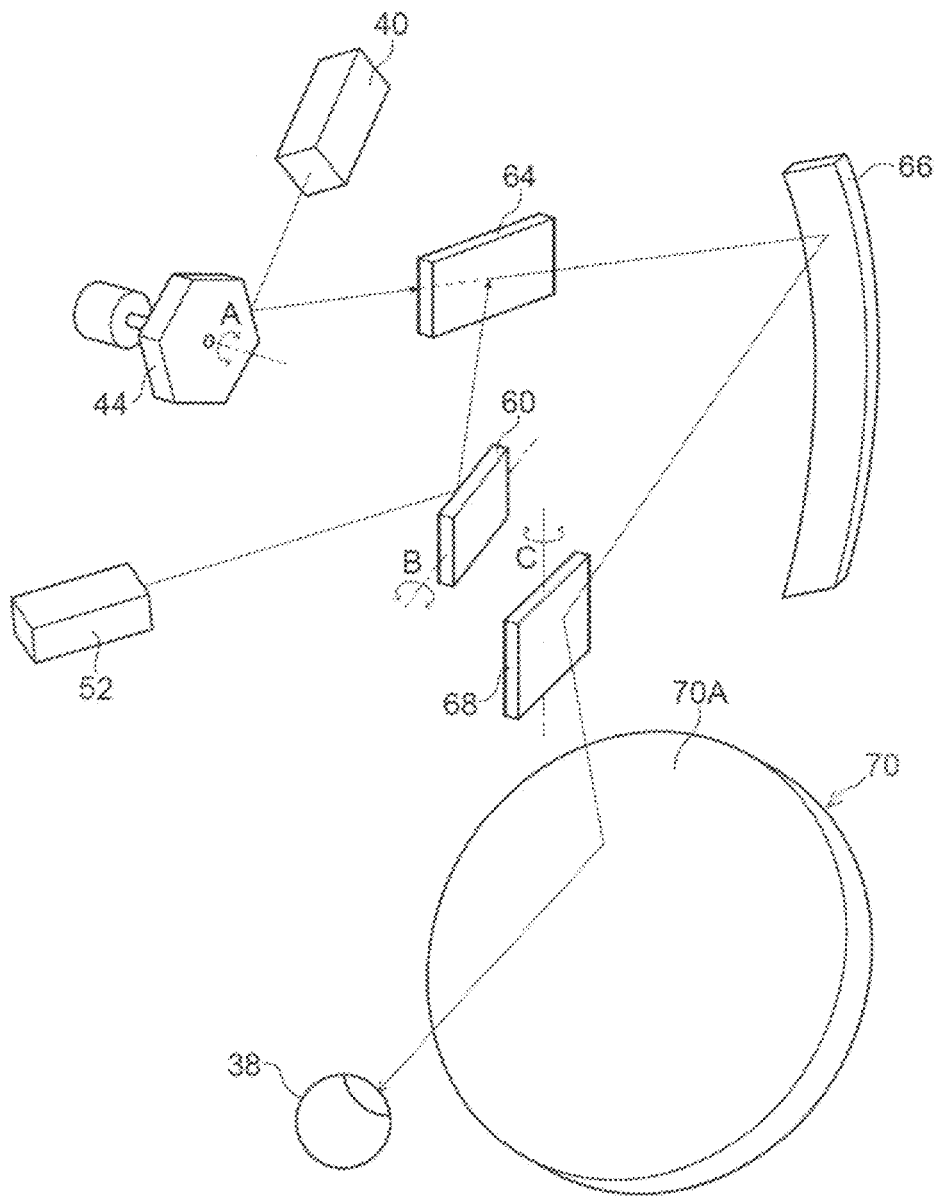
FIG. 3 is schematic perspective view illustrating an example configuration of the optical system in the embodiment that guides light emitted from respective light sources to the subject's eye.

The slit mirror 66 reflects incident emitted light toward the H-galvanometer mirror 68. The H-galvanometer mirror 68 reflects and sends the emitted light from the slit mirror 66 to a mirror face 70A of the ellipsoid mirror 70. Then, as illustrated in the example of FIG. 3, the H-galvanometer mirror 68 scans the emitted light in an X direction by rotationally oscillating in the arrow C direction on receiving drive force from the motor 48.

The ellipsoid mirror 70 guides emitted light to the retina by reflecting emitted light that was incident to the mirror face 70A. Emitted light guided to the retina is reflected by the retina. Then, the retina reflected light is guided to the dichroic mirror 64 in the shared optical system 36, along the same optical path as the emitted light. The dichroic mirror guides the first retina reflected light to the SLO unit 32 and guides the second retina reflected light to the OCT unit 34. Basic configuration of a retinal imaging optical system configured by two elliptical faces is similar to the configurations described in PCT application No. PCT/GB94/02465 (WO 95/13012) and PCT application No. PCT/GB2007/002208 (WO 2008/009877), the contents of which are incorporated herein by reference in their entirety.

During operation of the ophthalmic device 10-2, the controller 3 controls the first retinal image acquisition module 1 (specifically, the rotation of the H-galvanometer mirror 68 via drive signals transmitted to the motor 72, and the rotation of the polygon mirror 44 via drive signals transmitted to the motor 48 in the example of FIG. 2), and the second retinal image acquisition module 2-2 (specifically, the rotation of the H-galvanometer mirror 68 via drive signals transmitted to the motor 72, and the rotation of the V-galvanometer mirror 60 via drive signals transmitted to the motor 62 in the example of FIG. 2) such that the emitted light is scanned, via the slit mirror 66, the H-galvanometer mirror 68 and the ellipsoid mirror 70, across a common imaging region on the retina of the eye 38, for example in a raster pattern. The shape of the common imaging region on the retina is not limited and may, as in the present embodiment, be substantially rectangular (e.g. substantially square), or alternatively a line, for example. As noted above, however, the SLO light from the SLO unit 32 and the signal light from the OCT unit 34 need not be scanned across a common imaging region on the retina, and may instead be scanned across respective imaging regions that are different but nevertheless have a known positional offset relative to one another. For example, in other embodiments, the imaging region imaged by scanning the SLO light may be within the imaging region imaged by scanning the signal light, or vice versa, with the centers of the imaging regions in either case being coincident or offset relative to one another.

In the following, the region of the retina of the eye 38 imaged by the first retinal image acquisition module 1 (e.g. comprising the SLO unit 32, the shared optical system 36 and the SLO image generator 18 in the example of FIG. 2), across which region light from the first retinal image acquisition module 1 (the SLO light in that example) is scanned, is referred to as the "imaging region of the first retinal image acquisition module 1". Similarly, the region of the retina of the eye 38 imaged by the second retinal image acquisition module 2-2 (e.g. comprising the OCT unit 34, the shared optical system 36 and the OCT image generator 16 in the example of FIG. 2), across which region light from the second retinal image acquisition module 2-2 (the signal light in that example) is scanned, is referred to as the "imaging region of the second retinal image acquisition module 2-2".

As will be described in more detail below, by virtue of the arrangement of components in the shared optical system 36, the first retinal image acquisition module 1 is able to acquire an ultra-wide field (UWF) retinal image as a "reference retinal image", which can be regarded as a 'navigation map' for guiding movement of the imaging regions of the first and second retinal image acquisition modules 1 and 2-2 towards a desired region of the retina, as discussed in more detail below. More particularly, the controller 3 is configured to control movement of the polygon mirror 44 and the H-galvanometer mirror 68 in order to vary the optical path of the SLO light via the slit mirror 66 and the ellipsoid mirror 70 such that the light reflected from the retina and converted by the photo detector 46A produces, as the reference retinal image, up to a 200 degree scan of the retina as measured at the center O of the eye 38. In this way, the UWF retinal image can cover up to about 80% of the retina. The scanned area of the retina thus has an arc spanning an angle of up to 200 degrees about the (geometrical) center O of the subject's eye 38. In other embodiments, this angle may be up to 120 degrees, or up to 80 degrees, for example.

During the aforementioned changes to the locations of the imaging regions of the first and second retinal image acquisition modules 1 and 2-2, the first retinal image acquisition module 1 is configured to acquire one or more retinal images of regions of the retina whose areas are smaller than the reference imaging area imaged in the reference retinal image.

The device main body controller 13 controls operation of the device main body 12 by exchanging a variety of information with the device main body 12. Moreover, the device main body controller 13 generates a two-dimensional image indicating an aspect of the surface of the retina based on the SLO image signal obtained from the photo detector 46A. The device main body controller 13 also generates a three-dimensional (3D) image of the retina based on tomographic images generated from the OCT image signal from the line sensor 58.

In the present embodiment, the two-dimensional image obtained using the SLO unit 32 is broadly split into a chromatic image based on RG light and an achromatic image based on near-infrared light. Furthermore, tomographic images obtained using the OCT unit 34 are achromatic images. Two-dimensional images obtained using the SLO unit 32 and the tomographic images obtained using the OCT unit 34 may be displayed as still images, or may be displayed as a live view image.

The device main body controller 13 includes the controller 3, an OCT image generator 16, an SLO image generator 18, a user input interface (I/F) 20, at least one user input device 22, a display controller 24, a display 26, a communication I/F 28, and a bus line 30.

The controller 3, the OCT image generator 16, the SLO image generator 18, the user input I/F 20, the display controller 24, and the communication I/F 28 are connected to one another by the bus line 30. Accordingly, the controller 3 can exchange various items of information with the OCT image generator 16, the SLO image generator 18, the user input I/F 20, the display controller 24, and the communication I/F 28.

The controller 3 controls driving of the motors 48, 62 and 72 by controlling respective motor drive circuits (not illustrated in the drawings) corresponding to the motors 48, 62 and 72 via the communication I/F 28.

Furthermore, the controller 3 switches between lighting-up and lighting-out the light source 40A, adjusts the amount of light, changes the wavelength of light produced by the light source 40A, and the like, by controlling a light source drive circuit (not illustrated in the drawings) corresponding to the light source 40A via the communication I/F 28.

Furthermore, the controller 3 switches between lighting-up and lighting-out the SLD 50, adjusts the amount of light, changes the wavelength of light produced by the SLD 50, and the like, by controlling a SLD drive circuit (not illustrated in the drawings) corresponding to the SLD 50 via the communication I/F 28.

Furthermore, the controller 3 controls operation of the bandpass filter 40B, operation of the optical filter 46B, and operation of the reference mirror of the reference light optical system 54 via the communication I/F 28.

The at least one user input device 22 may, as in the present embodiment, include a keyboard and a mouse, and is operable to receive various instructions from a user. The user input device 22 may additionally or alternatively include a touch panel, or the like.

The user input devices 22 are connected to the user input I/F 20, and are arranged to output an instruction content signal indicating contents of the received instructions to the user input I/F 20. The controller 3 is configured to execute processing operations in accordance with the instruction content signal input from the user input I/F 20.

The display 26 may, for example, be an LCD or organic electroluminescence display (OELD). The display 26 is connected to the display controller 24. Under the control of the controller 3, the display controller 24 controls the display 26 so as to display on the display 26 a two-dimensional image obtained using the SLO unit 32 and a 3D representation of the retina based on tomographic images obtained using the OCT unit 34. Under the control of the controller 3, the display controller 24 can also display various screens, such as menu screens, by controlling the display 26.

The communication I/F 28 is connected to an electrical system of a device main body 12, and operates under the control of the controller 3 to govern exchange of various information between the controller 3 and the device main body 12.

The SLO image generator 18 acquires the SLO image signal from the photo detector 46A of the SLO unit 32 via the communication I/F 28, and may, as in the present embodiment, be a dedicated circuit configured to perform processing operations to generate a two-dimensional image based on the acquired SLO image signal.

The SLO image generator 18 may, as in the present embodiment, be configured to output frames of the generated two-dimensional images to the display controller 24 at a frame rate of typically tens of frames per second in the live tracking SLO feed. The display controller 24 may display the two-dimensional images input from the SLO image generator 18 on the display 26 as a live image in accordance with instructions by the controller 3. Moreover, the display controller 24 may display the two-dimensional images input from the SLO image generator 18 on the display 26 as still images, in accordance with instructions by the controller 3.

The OCT image generator 16 is configured to acquire the OCT image signal from the line sensor 58 of the OCT unit 34 via the communication I/F 28, and may, as in the present embodiment, be a dedicated circuit configured to perform processing operations to generate tomographic images based on the acquired OCT image signal.

The OCT image generator 16 may, as in the present embodiment, be configured to generate a 3D image of the retina by combining tomographic images (which may also be acquired at a rate of several tens of frames per second) using image processing techniques known to those skilled in the art. The tomographic images represent 'slices' through the retina at different depths from the retinal surface, and are combined by the OCT image generator 16 to generate a 3D image of the imaged portion of the retina. The display controller 24 may display the 3D image input from the OCT image generator 16 on the display 26, in accordance with instructions from the controller 3.

Although the OCT image generator 16 and the SLO image generator 18 are each implemented by a computer that includes a CPU, ROM, and RAM in the present embodiment, the technology disclosed herein is not limited thereto, and one or both of the OCT image generator 16 and the SLO image generator 18 may alternatively be implemented by field-programmable gate arrays (FPGA), or may be implemented by an application-specific integrated circuit (ASIC). Moreover, the OCT image generator 16 and the SLO image generator 18 may each be implemented by a combination of hardware configuration and software.

Figure 4:
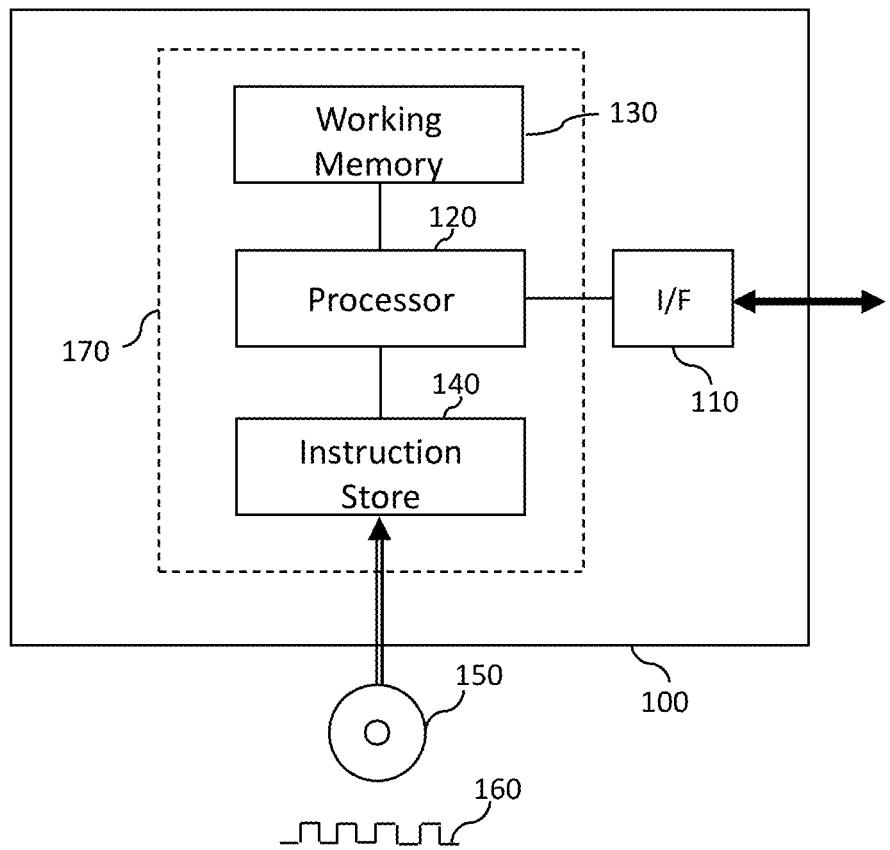
FIG. 4 is a block diagram illustrating an example of hardware configuration of the controller included in an ophthalmic device according to an embodiment.

FIG. 4 shows an exemplary implementation of the controller 3, in programmable signal processing hardware. The signal processing apparatus 100 shown in FIG. 4 comprises a communication I/F 110 for receiving data from, and transmitting control signals to, the bus 30. The signal processing apparatus 100 further comprises a processor (CPU) 120 for controlling the overall operation of the ophthalmic device 10-1 or 10-2, a working memory 130 (e.g. a random access memory) and an instruction store 140 storing computer-readable instructions which, when executed by the processor 120, cause the processor 120 to perform the processing operations hereinafter described to control the ophthalmic device 10-1 or 10-2. The instruction store 140 may comprise a ROM (e.g. in the form of an electrically-erasable programmable read-only memory (EEPROM) or flash memory) which is pre-loaded with the computer-readable instructions. Alternatively, the instruction store 140 may comprise a RAM or similar type of memory, and the computer-readable instructions can be input thereto from a computer program product, such as a computer-readable storage medium 150 such as a CD-ROM, etc. or a computer-readable signal 160 carrying the computer-readable instructions.

In the present embodiment, the combination 170 of the hardware components shown in FIG. 4, comprising the processor 120, the working memory 130 and the instruction store 140, is configured to implement the functionality of the controller 3, which will now be described in detail with reference to FIGS. 5 to 9.

The method by which the controller 3 of the present embodiment controls the ophthalmic device 10-2 to image the retina of the eye 38 will now be described with reference to FIGS. 5A and 5B.

Figure 5A:
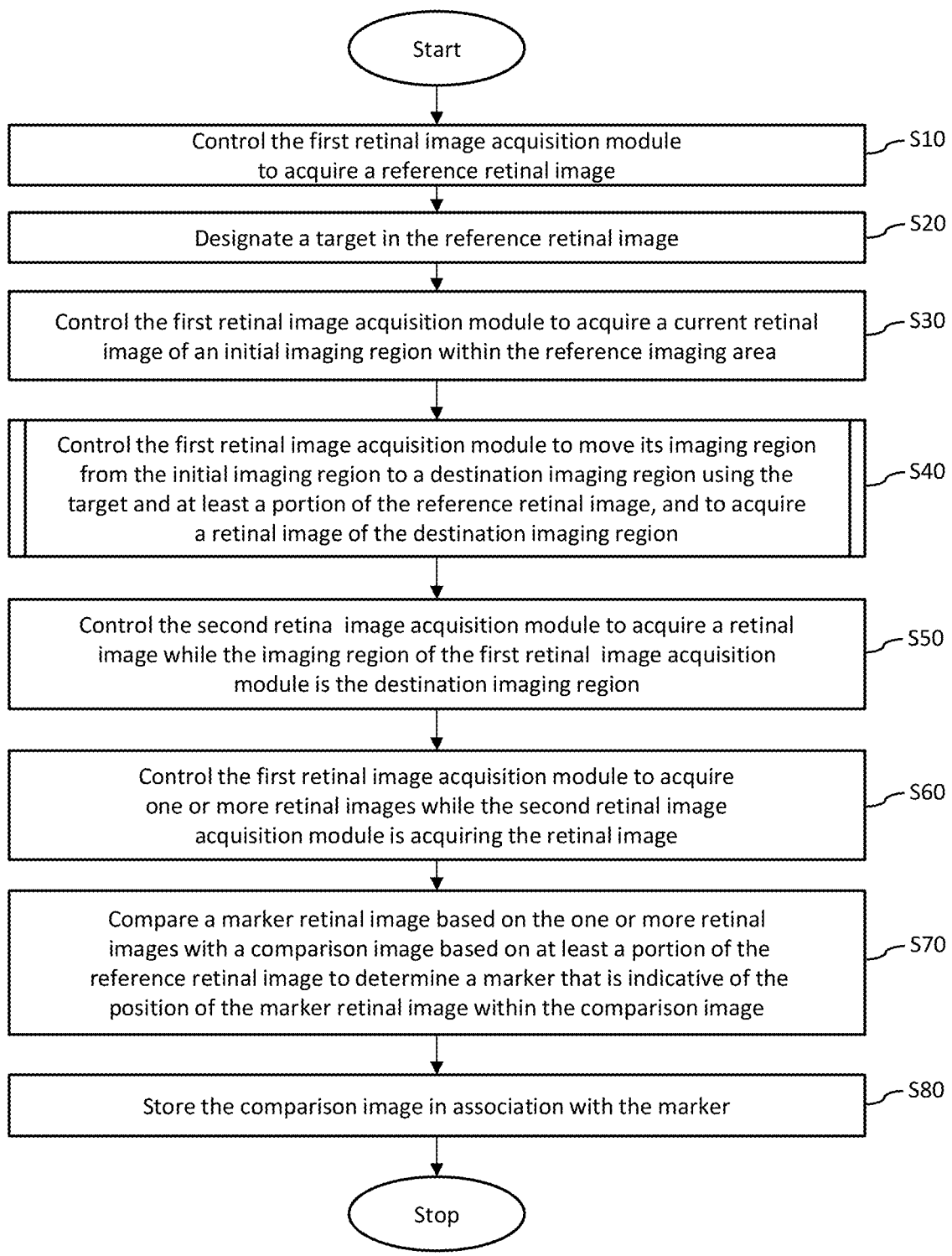
FIG. 5A is a flow diagram illustrating processes performed by the controller to control the ophthalmic device to image the retina of an eye.

Referring firstly to FIG. 5A, in process S10, the controller 3 controls the first retinal image acquisition module 1 to acquire the above-mentioned reference retinal image. Firstly, the patient is asked to rest their chin on a predetermined position of the ophthalmic device 10-2. A fixation target for fixing the gaze of the subject's eye 38 at a specific orientation is displayed on an LCD (not illustrated in the drawings) for displaying the fixation target. The gaze of the subject's eye 38 is fixed at a specific orientation due to the patient looking at the fixation target. Then, RG light is emitted from the light source 40A of the SLO unit 32, and the UWF retinal image of the subject's eye 38 is captured by operation of the SLO unit 32 and the shared optical system 36, under the control of the controller 3. An UWF RG-SLO image is acquired from the SLO image generator 18 as an example of the reference retinal image. It should be noted that near-infrared light from the light source 40A may alternatively be used to acquire an UWF IR-SLO image as the reference retinal image.

The patient's gaze direction is fixed during all of the subsequently imaging processes described below, and the ophthalmic device 10-2 is operable to image the different regions of the retina shown in the UWF reference retinal image without the patient changing the gaze direction. During these imaging processes, the controller 3 may monitor a live tracking SLO feed from the first retinal image acquisition module 1 to measure a motion metric that is indicative of the quality of the fixation, and generate signals for causing visual cues (e.g. changing colour of the fixation target, blinking the fixation target or changing a pattern of the fixation target) to be displayed to the subject for improving the fixation, as necessary.

Figure 7:
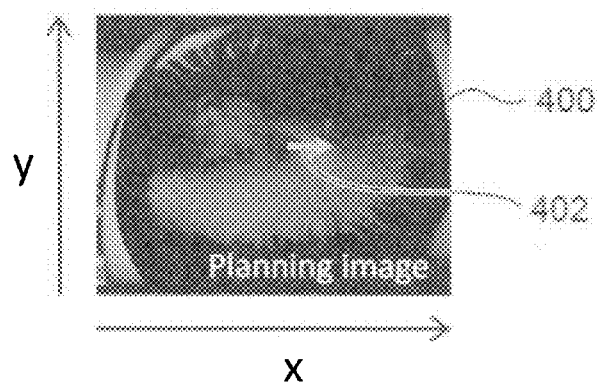
FIG. 7 is a schematic of a reference retinal image acquired by the first retinal image acquiring module of the embodiment.
Figure 8:
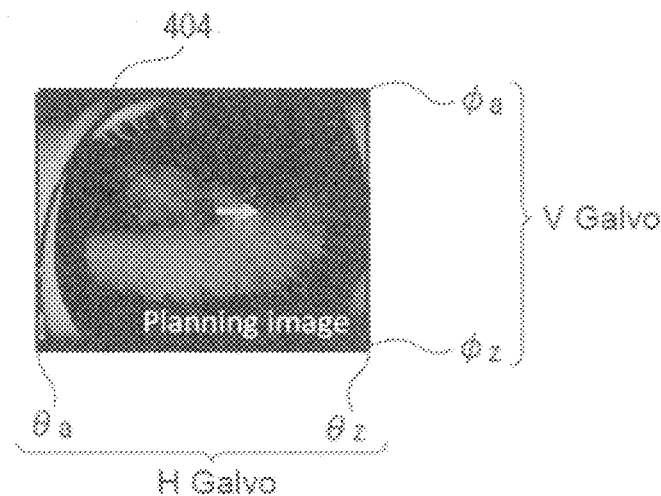
FIG. 8 is a schematic of a look-up table used by the controller to determine scan angles for the H-galvanometer mirror and V-galvanometer mirror of the ophthalmic device based on positions in the reference retinal image.

Under control of the controller 3, the display controller 24 controls the display 26 to display the acquired reference retinal image 400 (also referred to herein as a "planning image"), as illustrated in FIG. 7. The user is then able to view the UWF reference retinal image 400 (hereafter referred to as the "UWF retinal image 400") on the display 26, and identify a region of interest where, for example, a sign of a disorder is suspected and in which it would be desirable to perform OCT.

In process S20, the controller 3 designates a target in the UWF retinal image 400. The target may be designated by the controller 3 anywhere in the UWF retinal image 400 (including the peripheral portion of the retina), in one of a number of different ways. By way of an example, in the present embodiment, the user moves a cursor 402 overlaid on the displayed UWF retinal image 400, using the input device 22 (e.g. by moving the mouse). The user can designate a point of interest on the displayed UWF retinal image 400 in any desirable way, for example by clicking a button on the mouse while the cursor 402 is located at that point. The controller 3 designates the target by recording, for example, pixel locations in the UWF retinal image 400, which correspond to the location in the UWF retinal image 400 of the cursor 402 when the user designation (e.g. the mouse click) occurred. A region of the UWF retinal image 400 surrounding the target is thus selected for OCT imaging.

Although the target is thus designated based on the selection of a point on the displayed UWF retinal image 400 by the user in the present embodiment, the target may alternatively be designated based on the designation by the user of a line or two-dimensional region in the UWF retinal image 400 (e.g. by a 'click, drag and release' operation on the mouse to define e.g. a box in the UWF retinal image 400). For example, where a two-dimensional region in the UWF retinal image 400 is selected by the user, the controller 3 may designate the target as the coordinates (in the coordinate system of the of the UWF retinal image 400) of the centroid (geometrical center) of the two-dimensional region. The size of the two-dimensional region selected by the user may be used to define the size of the imaging area on the retina. The target may alternatively be designated automatically by the controller 3 using e.g. pattern-matching algorithms to identify one or more regions of interest (where features usually associated with a disorder are located) in the reference retinal image 400, or alternatively on the basis of received or stored 'marker' as described below.

In process S30, the controller 3 controls the first retinal image acquisition module 1 to acquire a current retinal image of an initial imaging region of the retina that is within the reference imaging area. For this purpose, the controller 3 may, as in the present embodiment, employ a look-up table (as shown at 404 in FIG. 8) stored in the instruction store 140, which correlates pixel locations in the UWF retinal image 400 with corresponding inclination angles θ of the H-galvanometer mirror (H-Galvo) 68 and ϕ of the V-galvanometer mirror (V-Galvo) 60 that were set while image information at those points was acquired during the imaging process (S10). Where such a look-up table is used, the controller 3 may look up the scan angles θ and ϕ associated with a pre-stored point that is closest to the target in the reference retinal image, and control the drive of the H-Galvo 68 and V-Galvo 60 to deflect the SLO light across angular ranges centered on those scan angles, the angular ranges of the scan defining the size of the imaged region of the retina. In this way, the emitted light may be scanned over an imaging region on the retina which is close to the intended imaging region, corresponding to that centered on the designated target. For a more precise setting of the initial imaging regin, the scan angles may be determined by extrapolating between the values in the look-up table. It should be noted, however, that such initial setting of the scan angles to image the initial imaging region within the reference imaging area may be omitted, and the scan angles θ and ϕ may alternatively be set to any other values that allow an initial imaging region within the reference imaging area to be imaged.

The controller 3 then uses target 408, and the UWF retinal image 400 as a 'global map', to move the imaging region of the first retinal image acquisition module 1 from the initial imaging region to a destination imaging region on the retina, and controls the first retinal image acquisition module 1 to acquire a retinal image of the destination imaging region. Along the way, the controller 3 may use one or more retinal images acquired by the first retinal acquisition module 1 to 'land-mark' the current position(s) of the images on the global map, allowing it to determine any further adjustments to the location of the imaging region that might be required to arrive at the destination imaging region. The controller 3 can thus move the imaging region to the destination imaging region of interest in a step-wise manner, without the need for scan location mappings of the kind present in the look-up table 404, and without being influenced by scan location errors due to systematic variations in the optical imaging system and fixation errors. More particularly, in process S40, the controller 3 may control the first retinal image acquisition module 1 to acquire a retinal image of a destination imaging region of the first retinal image acquisition module 1 by performing at least once the sequence of processes S42 to S48 illustrated in FIG. 5B, as follows.

In process S42, the controller 3 determines the position, within the UWF retinal image 400, of the current retinal image acquired in process S30 by comparing the current retinal image (shown at 406 in FIG. 9) with the UWF retinal image 400. The controller 3 may, as in the present embodiment, attempt to match retinal features (including, e.g. vasculature) in the current retinal image 406 with the same retinal features somewhere in the UWF retinal image 400 by calculating a cross-correlation between the current retinal image 406 and the UWF retinal image 400 and determining, based on the calculated cross-correlation, the location of the current retinal image 406 within the UWF retinal image 400.

In process S44, the controller 3 compares the position of the current retinal image 406 within the UWF retinal image 400 with a position of the target (shown at 408 in FIG. 9) within the UWF retinal image 400. Based on the result of this comparison, the controller 3 determines an adjustment to move the current imaging region of the first retinal image acquisition module 1 closer to a target on the retina corresponding to the target 408 in the UWF retinal image 400. This adjustment may be determined, for example, by calculating the differences in the X and Y directions shown in FIG. 9 between the the position of the target 408 and the position of the current retinal image 406 and, based on the signs of the calculated differences, setting adjustments to the angles of the H-Galvo 68 and V-Galvo 60 for altering the respective angles by a predetermined amount and in a direction determined by the signs of the calculated differences. For example, with the locations of the target 408 and the current retinal image 406 shown in FIG. 9, the adjustment would be +Δθ and +Δϕ, where Δθ and Δϕ are the predetermined angular adjustments for the H-Galvo 68 and V-Galvo 60, which may, but need not, be the same. The controller 3 is thus able to determine an adjustment for nudging the scan angles so as to move the imaging region of the first retinal image acquisition device 1 in a direction closer to the target. The controller 3 may, and in the present embodiment, also control the display controller 24 to generate display data for displaying on the display 26 an indication of the adjustment determined in process S50.

In process S46, the controller 3 uses the determined adjustment to control the first retinal image acquisition module 1 to set the imaging region thereof to another imaging region within the UWF retinal image 400, which then becomes the current imaging region. The controller 3 controls the first retinal image acquisition module 1 to set the imaging region to the other imaging region by generating and transmitting control signals to motors 48 and 72 to cause the polygon mirror 44 and H-Galvo 68 to move in way that projects the SLO light along a range of optical paths through the shared optical system 36 that are intended to end on the other imaging region.

Figure 9:
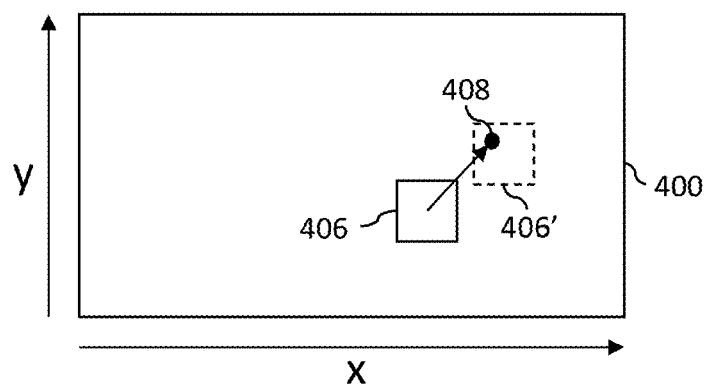
FIG. 9 illustrates two retinal images acquired by the first retinal image acquiring module of the embodiment that have been registered with the reference retinal image.

In process S48, the controller 3 controls the first retinal image acquisition module 1 to acquire, as the retinal image of the destination imaging region, a retinal image 406' of the imaging region set in process S46. As illustrated in FIG. 9, the location of image 406' is closer to the target location 408 than is the location of image 406 of the initial imaging region.

Referring again to FIG. 5A, in process S50, the controller 3 controls the second retinal image acquisition module 2-2 to acquire a retinal image while the imaging region of the first retinal image acquisition module 1 is the destination imaging region set in process S46. By way of an example, in the present embodiment, the controller 3 controls the second retinal image acquisition module 2-2 to acquire a 3D image of the current imaging region of the second retinal image acquisition module 2-2, which is the same as the destination imaging region set in process S46 in the present embodiment, by acquiring a plurality of tomographic images of the current imaging region (over a period of about 1-2 seconds) and processing the tomographic images by the OCT image generator 16 to generate the 3D image.

During the acquisition of the plurality of tomographic images by the second retinal image acquisition module 2-2, the first retinal image acquisition module 1 operates in a live tracking mode in process S60 to acquire one or more further images of the retina as "post-registration image(s)" while the imaging region of the first retinal image acquisition module 1 remains set at that determined in process S46.

In process S70, the controller 3 generates a marker retinal image based on the one or more retinal images, and also generates a comparison image based on at least a potion of the UWF retinal image 400. The marker retinal image may, as in the present embodiment, correspond to a single post-registration image acquired by the first retinal image acquisition module 1 while the second retinal image acquisition module 2-2 is acquiring the plurality of tomographic images, or may be obtained by processing two or more post-registration images acquired by the first retinal image acquisition module 1 while the second retinal image acquisition module 2-2 is acquiring the tomographic images, for example by calculating an average of two or more of the post-registration images, or selecting an image from a plurality of post-registration images according to a selection criterion such as image quality. The comparison image may, as in the present embodiment, correspond to the entire UWF retinal image 400, or may alternatively be only a portion of the UWF retinal image 400 (e.g. covering an area of the retina in which retinal scans are most likely to be made). In process S70, the controller 3 compares the marker retinal image with the comparison image 400 and, based on the comparison, generates a marker that is indicative of the position of the marker retinal image within the comparison image. The controller 3 may generate the maker on the basis of a calculated cross-correlation between the marker retinal image and the comparison image, for example.

The controller 3 may then store (in optional process S80) the marker in association with the comparison image. The marker may be stored not only in association with the comparison image but additionally or alternatively in association with one or more of: (i) the (3D) retinal image acquired by the second retinal image acquisition module 2-2; (ii) at least one of the one or more post-registration retinal images acquired by the first retinal image acquisition module 1; (iii) the marker retinal image; (iv) the reference retinal image 400; and (v) a clipped region of the reference retinal image 400, wherein the clipped region is positioned at the determined position of the marker retinal image within the reference retinal image 400, and may be same size as (or preferably larger than) the post-registration image(s).

The sequence of processes S42 to S48 may be repeated by the controller 3 in its control of the ophthalmic device 10-2 to image the retina of the eye 38, so that a sequence of retinal images is acquired by the first retinal image acquisition module 1 between the acquisition of the retinal image of the initial imaging region and the acquisition of the retinal image of the destination imaging region, with the imaging region of each image in the sequence being closer to the destination imaging region than the imaging region of the preceding image in the sequence. An example of a condition used to determine when to stop repeating processes S42 to S48 is provided in the following description of FIGS. 10A to 10C. It should be noted that processes S42 to S48 may alternatively be performed a predetermined number of times.

During the acquisition of the 3D retinal image by the second retinal images acquisition module 2-2, or during the acquisition of a subsequent 3D retinal image by the second retinal images acquisition module 2-2, the controller 3 may generate a second marker retinal image based on another one or more retinal images to those acquired in process S60, and compare the second marker retinal image with a second comparison image that is based on at least a portion of the UWF retinal image 400 to determine a second marker that is indicative of the position of the second marker retinal image within the second comparison image. The controller 3 may then determine a relative offset between the positions of the first and second marker retinal images in the UWF retinal image 400, and store the determined relative offset and/or display the determined relative offset on the display 26.

The process by which the controller 3 controls the ophthalmic device 10-1 of FIG. 1A is largely as described above with reference to FIGS. 5A and 5B. The processes performed by the controller 3 in this embodiment are summarised in FIG. 6. Processes S10 to S40 and S70 in FIG. 6 are the same as those described above with reference to FIGS. 5A and 5B, and their description will therefore not be repeated. In process S50' in FIG. 6, however, the controller 3 controls the illumination module 2-1 to illuminate the illumination region of the retina while the imaging region of the first retinal image acquisition module 1 is set to the destination imaging region, and in process S60', the controller controls the first retinal image acquisition module 1 to acquire one or more retinal images while the illumination module 2-1 is illuminating the illumination region of the retina.

Figure 10A:
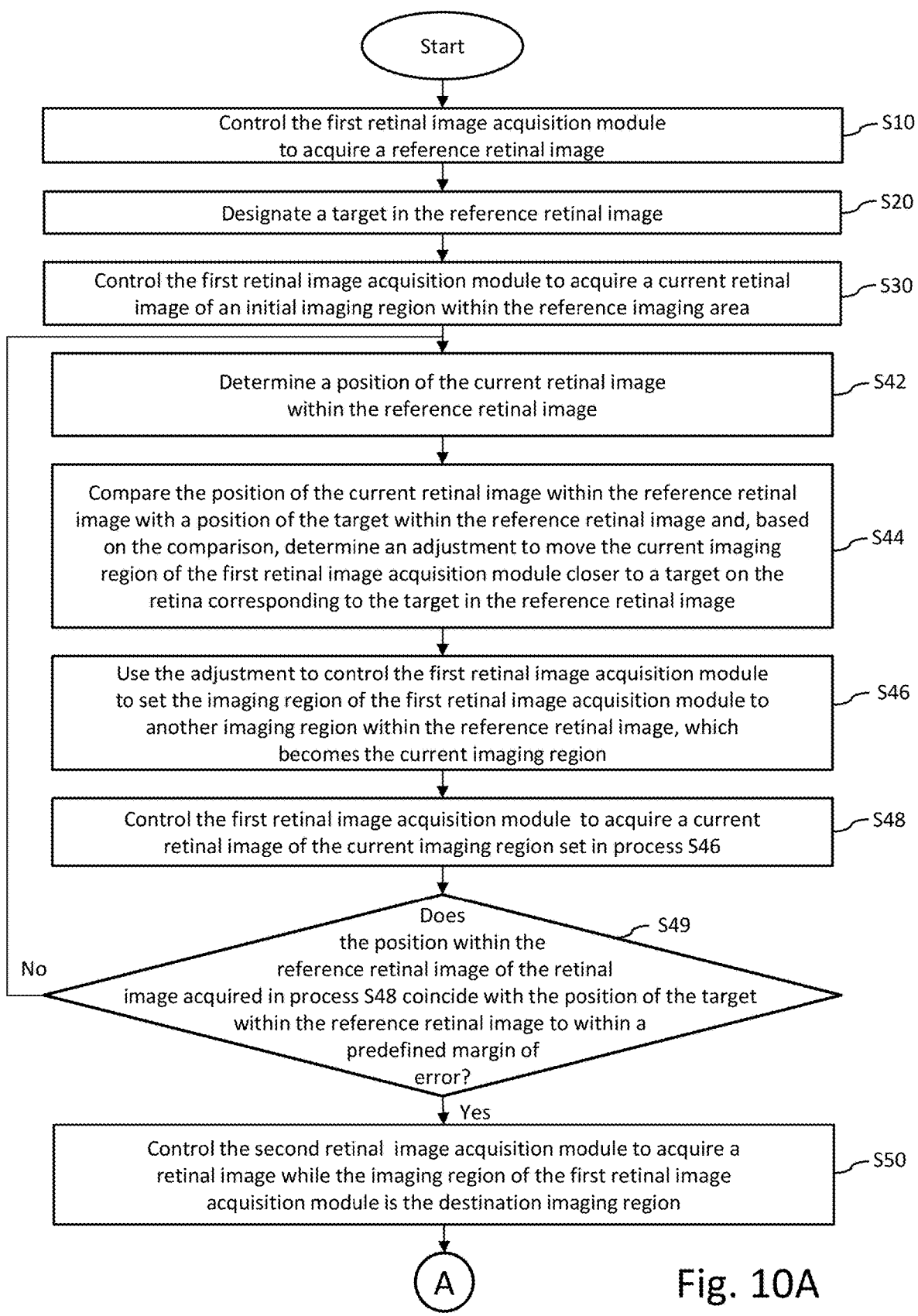
Figure 10B:
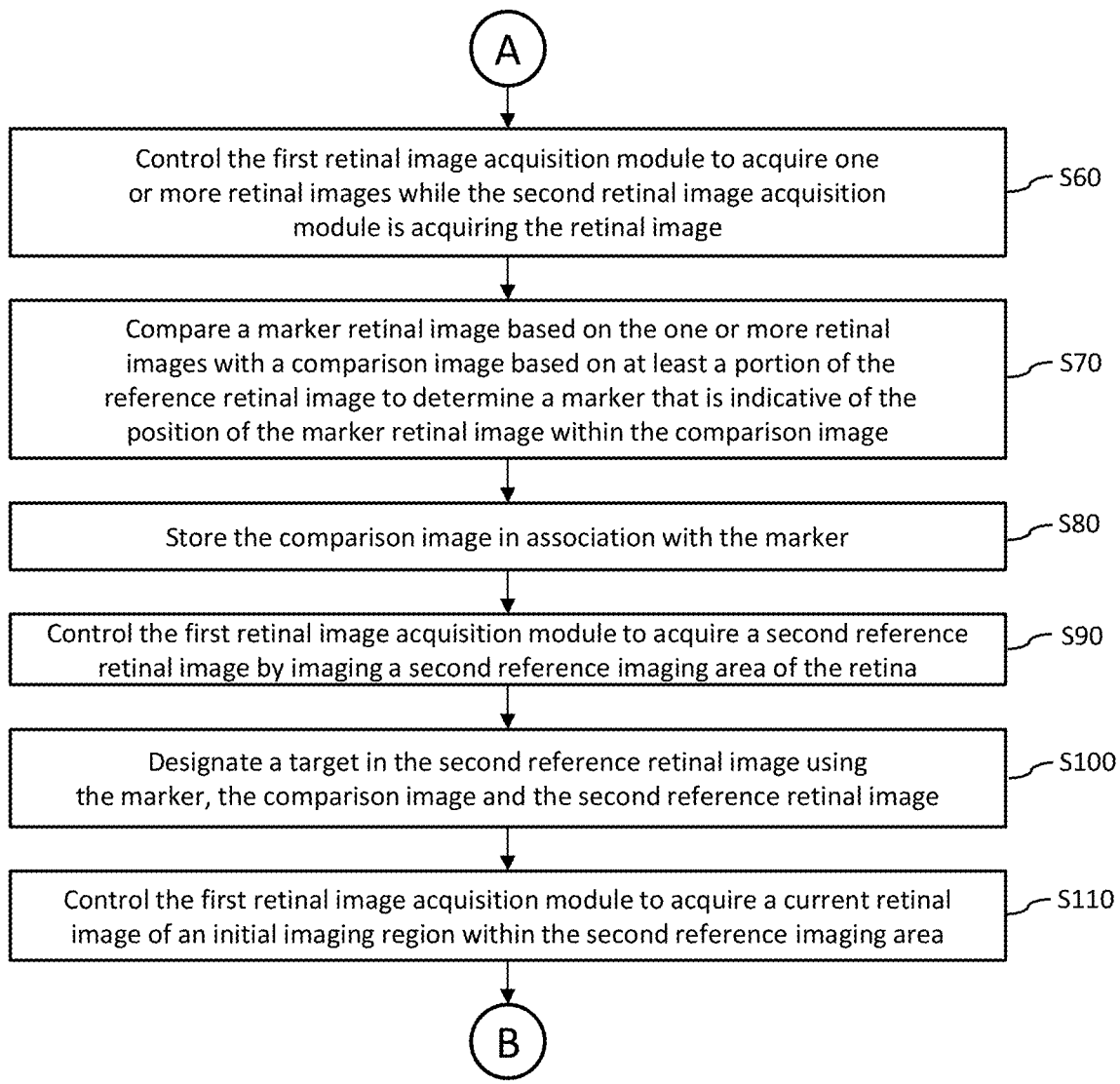

A method by which the controller 3 may control the ophthalmic device 10-2 to acquire, by the second retinal image acquisition module 2-2, a first 3D image of a region of the retina as a first retinal image acquired by the second retinal image acquisition module 2-2, as well as a second 3D image of the region of the retina as a second retinal image acquired by the second retinal image acquisition module 2-2 in a subsequent repeat scan of the patient's eye, will now be described with reference to FIGS. 10A to 10C. This method may allow the 3D images of substantially the same region of the retina to be obtained in the repeat scan, even if a different optical scan-head is used for performing the repeat scan.

Figure 5B:
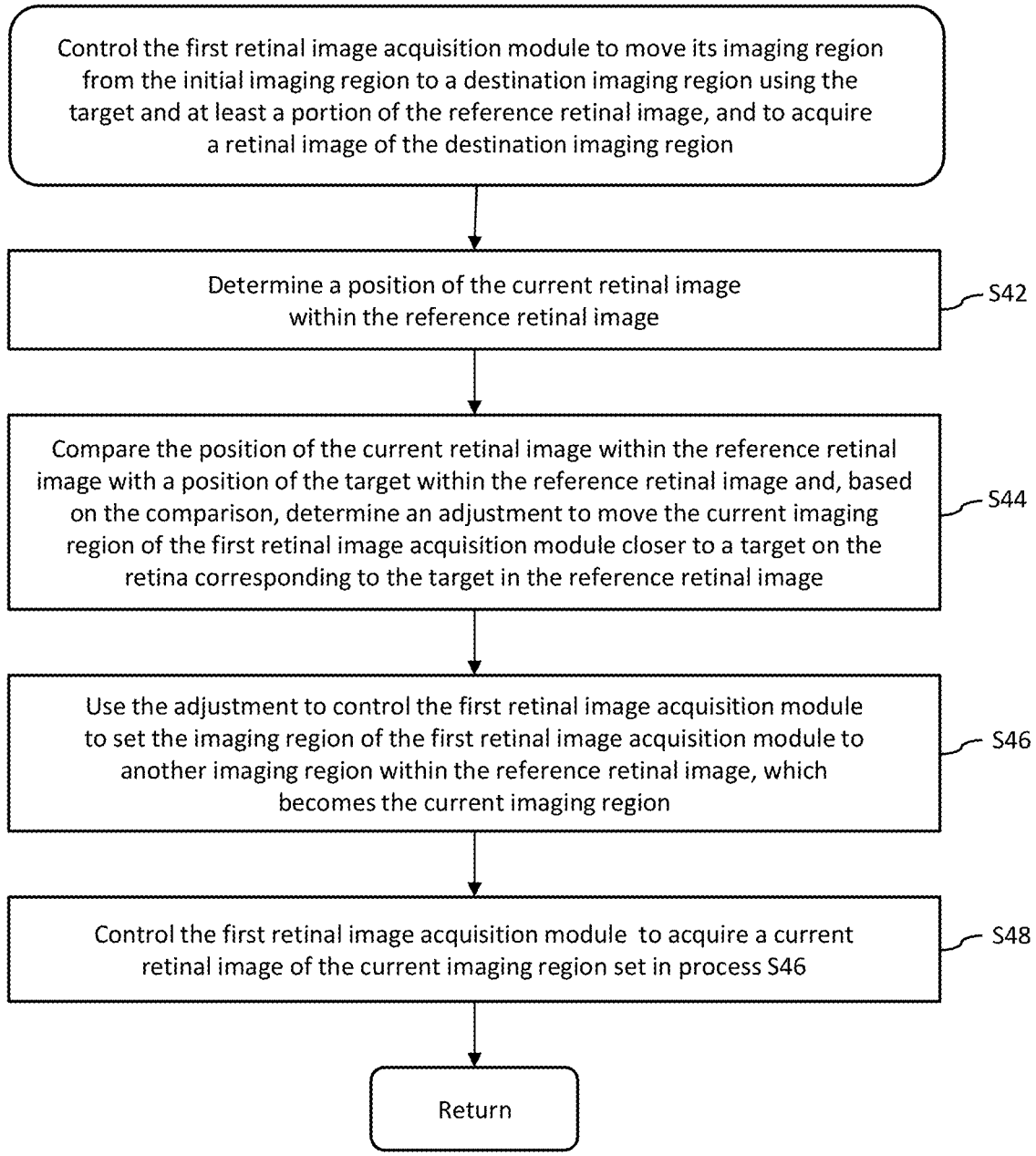
FIG. 5B is a flow diagram illustrating how process S40 in FIG. 5A may be performed.
Figure 6:
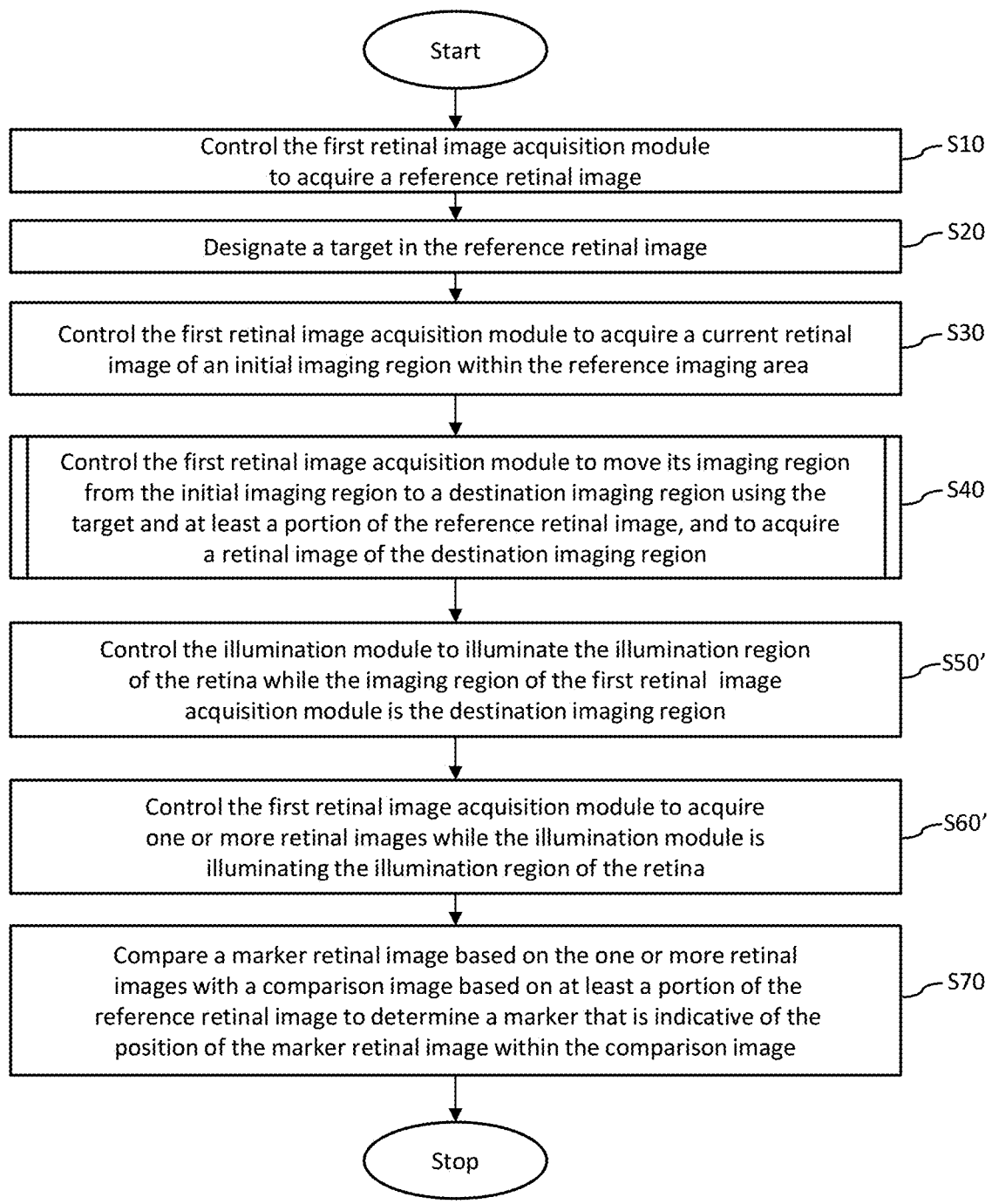
FIG. 6 is a flow diagram illustrating processes performed by the controller to control the ophthalmic device to illuminate the retina of an eye.

Processes S10 to S80 in FIGS. 10A and 10B are the same as processes S10 to S80 in FIGS. 5A and 5B, and their description will therefore not be repeated here. A decision may be made (in process S49) whether to repeat the sequence of processes S42 to S48, specifically by the controller 3 determining whether the position within the UWF retinal image 400 of the retinal image acquired in process S48 coincides with the position of the target 408 within the UWF retinal image 400 to within a predefined margin of error, i.e. whether the distance between the position within the UWF retinal image 400 of the retinal image acquired in process S48 and the position of the target 408 within the UWF retinal image 400 is less than a predetermined distance. If the position of the retinal image acquired in process S48 does not coincide with the position of the target 408 to within the predefined margin of error, the method may loop back to process S42, otherwise the method may proceed to process S50 and then to processes S60 to S80 (see FIG. 10B), as described above. It should be noted, however, that such closed-loop adjustment of the imaging region of the first retinal image acquisition module 1 is optional, and the sequence of processes S42 to S48 is not repeated in some embodiments.

Where the sequence of processes S42 to S48 is performed more than once, the controller 3 may, as in the present embodiment, determine the adjustment to the location of the current imaging region in the second and any subsequent performance of process S44 based on the one or more adjustments determined in one or more of the previous performances of process S44. The controller 3 may thus base its determination of an adjustment to the location of the current imaging region on the response to one or more previous adjustments. For example, the change in the position within the UWF retinal image 400 of the retinal image acquired by the first retinal image acquisition module 1 as a consequence of the previous adjustment (e.g. $+\Delta\theta$ and $+\Delta\phi$) may be used to establish a relation between the adjustment amount and its effect in moving the position of the retinal image within the UWF retinal image 400, so that a different adjustment amount (e.g. $+3\Delta\theta$ and $+5\Delta\phi$) may subsequently be used to move the position of the retinal image within the UWF retinal image 400 closer to the target 408 than would the previously used adjustment amount ($+\Delta\theta$ and $+\Delta\phi$).

Referring to FIG. 10B, in process S90, the controller 3 controls the first retinal image acquisition module 1 to acquire a second UWF retinal image as an example of a second reference retinal image, by imaging a second reference imaging area of the retina. This process is similar to process S10, and may be performed on the patient at a later check-up.

In process S100, the controller 3 designates a target in the second UWF retinal image using the marker, the comparison image and the second UWF retinal image. The controller 3 may designate the target in the second UWF retinal image by comparing the comparison image with the second UWF retinal image to determine a positional relationship of retinal features in the comparison image and the second reference retinal image (in other words, a translational and/or rotational offset between corresponding features in the two UWF retinal images), and setting the target in the second reference retinal image using the determined positional relationship and the marker (for example, by applying the determined offset(s) to the position indicated by the marker in order to determine the position in the second UWF retinal image that corresponds to the indicated position in the first UWF retinal image). In this process, the controller may performing a pattern-matching process to attempt to match retinal features (e.g. vascular features) in the comparison image with the same features somewhere in the second UWF retinal image, by, for example, calculating a cross-correlation between the comparison image and the second UWF retinal image and determining, from the location of a peak in the resulting cross-correlation values, the relative offset between the two images.

In process S110, the controller 3 controls the first retinal image acquisition module 1 to acquire a current retinal image of an initial imaging region within the second UWF retinal image.

The controller 3 then controls the first retinal image acquisition module 1 to acquire a retinal image of a destination imaging region within the second reference imaging area by performing at least once processes S120 to S150 illustrated in FIG. 10C, as follows.

In process S120, the controller 3 determines a position of the current retinal image within the second UWF retinal image by comparing the current ocular retinal image with the second UWF retinal image.

In process S130, the controller 3 compares the position of the current retinal image within the second UWF retinal image with a position of the target within the second UWF retinal image. Based on the result of this comparison, the controller 3 determines an adjustment to move the current imaging region of the first retinal image acquisition module 1 closer to a target on the retina corresponding to the target in the second UWF retinal image.

In process S140, the controller 3 uses the adjustment to control the first retinal image acquisition module 1 to set the imaging region of the first retinal image acquisition module 1 to another imaging region within the second UWF retinal image, which then becomes the current imaging region.

In process S150, the controller 3 controls the first retinal image acquisition module 1 to acquire a current retinal image of the current imaging region set in process S140.

The retinal image of the destination imaging region within the second UWF retinal image is the retinal image acquired in the final performance of process S150.

The details of processes S120 to S150 are substantially the same as those of processes S42 to S48, which have been described above with reference to FIG. 10A.

Optionally, the sequence of processes S120 to S150 may be repeated a predetermined number of times or, as in the example of FIG. 10C, until the position within the second UWF retinal image of the retinal image acquired in process S150 coincides with the position of the target within the second UWF retinal image to within a second predefined margin of error, which may be different from the margin of error used in process S49. In embodiments like the present, in which the sequence of processes S120 to S150 is performed more than once, a decision whether to repeat the sequence of processes S120 to S150 is made in process S160, specifically by the controller 3 determining whether the position of the retinal image acquired in process S150 coincides with the position of the target within the second UWF retinal image to within the second predefined margin of error. If the position of the retinal image acquired in process S150 does coincide with the position of the target within the second UWF retinal image to within the second predefined margin of error, the method proceeds to process S170, otherwise the method loops back to process S120. As noted above, such closed-loop adjustment of the imaging region of the first retinal image acquisition module 1 is optional, so that the sequence of processes S120 to S150 is not repeated in some embodiments.

In process S170, the controller 3 controls the second retinal image acquisition module 2 to acquire, as the second retinal image, a 3D image of the retina in the imaging region of the second retinal image acquisition module 2 while the imaging region of the first retinal image acquisition module 1 is the imaging region set in the final performance of process S140. The ophthalmic device 10-2 thus acquires a second 3D image of the substantially the same portion of the retina as that obtained in the previous examination of the eye 38. Owing to the use by the controller 3 of the marker and comparison image from the previous examination, and an UWF retinal image acquired during the second examination, the ophthalmic device 10-2 is able to navigate to the region of the retina imaged during the previous examination—without needing to rely on mappings of the kind stored in the look-up table 404—and thus to acquire a second 3D image of this region.

During the acquisition of the plurality of tomographic images by the second retinal image acquisition module 2-2, the first retinal image acquisition module 1 operates in a live tracking mode in process S180 to acquire one or more further images of the retina as post-registration image(s) while the imaging region of the first retinal image acquisition module 1 remains set at that determined in process S140.

In process S190, the controller 3 generates a second marker retinal image based on the one or more further retinal images acquired in process S180, and also generates a second comparison image based on at least a portion of the second UWF retinal image. The second marker retinal image may, as in the present embodiment, correspond to a single post-registration image acquired by the first retinal image acquisition module 1 while the second retinal image acquisition module 2-2 is acquiring the plurality of tomographic images in process S170, or may be obtained by processing two or more post-registration images acquired by the first retinal image acquisition module 1 while the second retinal image acquisition module 2-2 is acquiring the tomographic images, for example by calculating an average of two or more of the post-registration images, or selecting an image from a plurality of post-registration images according to a selection criterion such as image quality. The second comparison image may, as in the present embodiment, correspond to the entire second UWF retinal image, or may alternatively be only a portion of the second UWF retinal image (e.g. covering an area of the retina in which retinal scans are most likely to be made). In process S190, the controller 3 compares the second marker retinal image with the second comparison image 400 and, based on the comparison, generates a second marker that is indicative of the position of the second marker retinal image within the second comparison image. The controller 3 may generate the second maker by finding the peak in the cross-correlation between the second marker retinal image and the second comparison image, for example.

The controller 3 may then store (in process S200) the second marker in association with the second comparison image. The second marker may be stored not only in association with the second comparison image but additionally or alternatively in association with one or more of: (i) the second (3D) retinal image acquired by the second retinal image acquisition module 2-2; (ii) at least one of the one or more further post-registration retinal images acquired by the first retinal image acquisition module 1; (iii) the second marker retinal image; and (iv) a clipped region of the second UWF retinal image, wherein the clipped region is positioned at the determined position of the second marker retinal image within the second UWF retinal image, and may be same size as (or preferably larger than) the post-registration image(s).

During the acquisition of the second 3D retinal image by the second retinal images acquisition module 2-2, or during the acquisition of a further 3D retinal image by the second retinal images acquisition module 2-2, the controller 3 may generate a third marker retinal image based on another one or more retinal images to those acquired in process S180, and compare the third marker retinal image with a third comparison image that is based on at least a portion of the second UWF retinal image to determine a third marker that is indicative of the position of the third marker retinal image within the third comparison image. The controller 3 may then determine a relative offset between the positions of the second and third marker retinal images in the second UWF retinal image, and store the determined relative offset and/or display the determined relative offset on the display 26.

[Modifications and Variations]

Many modifications and variations can be made to the embodiments described above.

In the embodiments explained above, the polygon mirror 44 arranged to scan in the Y direction, and the V-galvanometer mirror 60 arranged to scan in the Y direction, are disposed at the light incidence side of the dichroic mirror 64. However, the dichroic mirror 64 may be disposed in a position separated in the optical axis direction from the focal point of the slit mirror 66, and the polygon mirror 44 or the V-galvanometer mirror 60 that scans in the Y direction may be disposed at the focal point position of the slit mirror 66. In such cases, the polygon mirror 44 or the V-galvanometer mirror 60 functions as a shared scanning optical system employed during SLO image acquisition and OCT image acquisition.

Furthermore, although an example has been described in which a shared optical axis, along which light for SLO and light for OCT passes, is generated by the dichroic mirror 64, a beam splitter such as a polarizing beam splitter or an optical member such as a half-mirror may be employed instead of the dichroic mirror 64.

Figure 11:
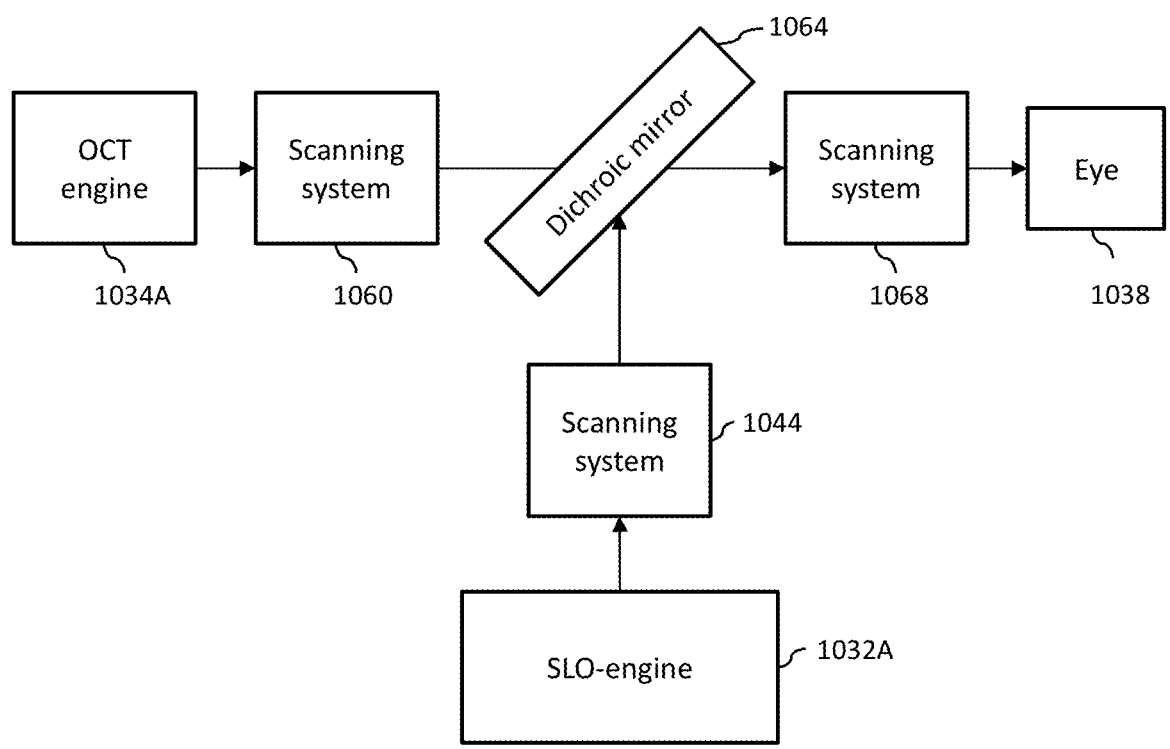
FIG. 11 is a schematic illustration of the optical system of the ophthalmic device of the embodiment.

In the above embodiments, the polygon mirror 44 and the V-galvanometer mirror 60 are disposed at the light incidence side of the dichroic mirror 64, and the H-galvanometer mirror 68 for X direction scanning, shared by SLO and OCT, is disposed at the light emission side of the dichroic mirror 64, as illustrated in FIG. 2. FIG. 10 illustrates a configuration corresponding to the SLO unit 32, the OCT unit 34, and the shared optical system 36 illustrated in FIG. 1. As illustrated in FIG. 11, a device main body includes a dichroic mirror 1064, an SLO engine 1032A, and an OCT engine 1034A. A scanning system 1044 is disposed between the dichroic mirror 1064 and the SLO engine 1032A. Further, another scanning system 1060 is disposed between the dichroic mirror 1064 and the OCT engine 1034A. A further scanning system 1068 is disposed between the dichroic mirror 1064 and a subject's eye 1038.

Note that the scanning system 1044 corresponds to the polygon mirror 44, and the SLO engine 1032A is a portion obtained by removing the polygon mirror 44 from the SLO unit 32 in FIG. 1. The scanning system 1060 corresponds to the V-galvanometer mirror 60, and the OCT engine 1034A is a portion obtained by removing the V-galvanometer mirror 60 from the OCT unit 34 in FIG. 2. The scanning system 1068 corresponds to the H-galvanometer mirror 68.

The following modifications can be can be made to the scanning optical system.

Figure 12:
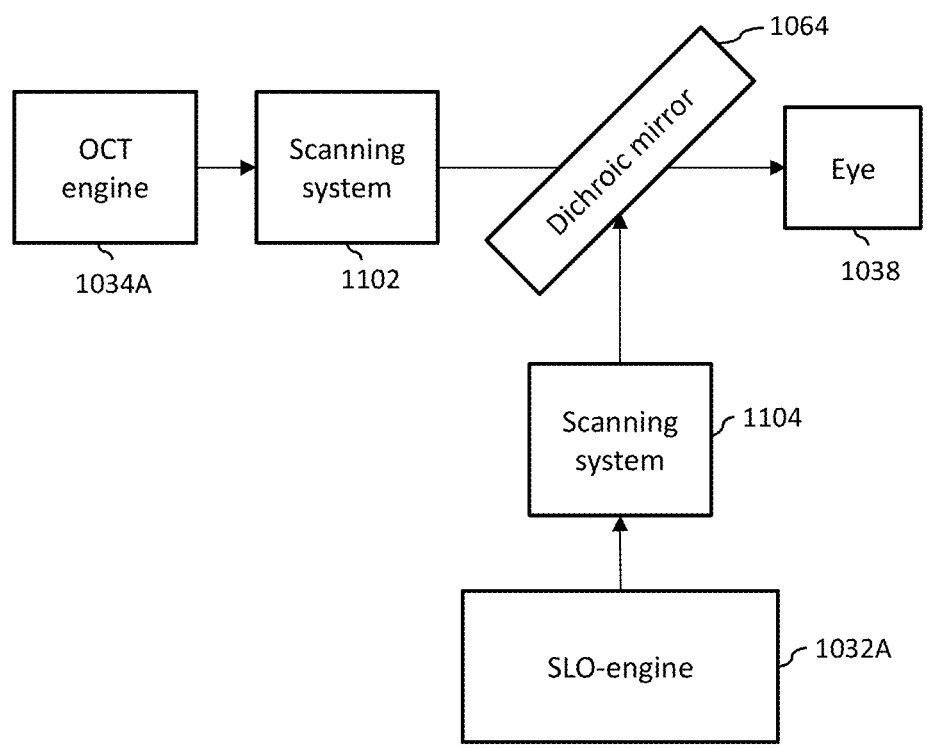
FIG. 12 is a schematic illustration of the optical system of the ophthalmic device of a first variant of the embodiment.

FIG. 11 is a schematic illustration of the optical system of the ophthalmic device of a first variant of the embodiment. As illustrated in FIG. 12, a two-dimensional scanning optical system 1104 for SLO is disposed on one light incidence side (the SLO engine 1032A side) of the dichroic mirror 1064, and a two-dimensional scanning optical system 1102 for OCT is disposed at another light incidence side (the OCT engine 1034A side) of the dichroic mirror 1064.

Figure 13:
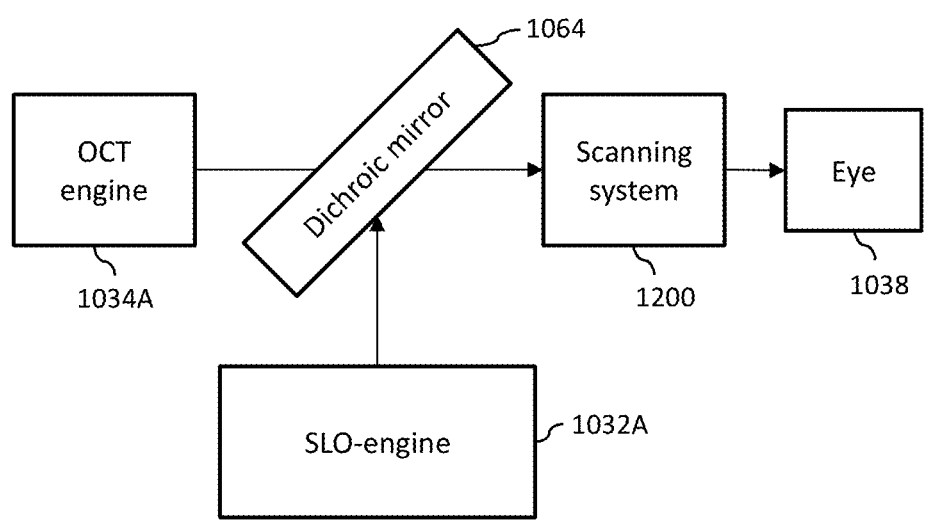
FIG. 13 is a schematic illustration of the optical system of the ophthalmic device of a second variant of the embodiment.

FIG. 12 is a schematic illustration of the optical system of the ophthalmic device of a second variant of the embodiment. As illustrated in FIG. 13, a shared two-dimensional scanning optical system 1200, employed by SLO and OCT, is disposed at the light emission side of the dichroic mirror 1064.

Furthermore, in the all of the scanning optical systems explained above, similar scanning can be performed by exchanging the X direction with the Y direction.

Although explanation has been given regarding examples in which an ellipsoid mirror is employed as an optical member that relays the scanning, another concave mirror such as a parabolic mirror may be employed, or an optical member such as a lens may be employed instead of a concave mirror. An optical member that includes plural focal points may be employed as the optical member that relays the scanning. In such cases, the positional relationship between the optical member, the scanning optical system, and the subject's eye may adopt the following aspects.

In a first aspect, the subject's eye is disposed at one focal point position f1, and a shared two-dimensional scanning optical system, employed by SLO and OCT, is disposed at another one focal point position f2.

In a second aspect, the subject's eye is disposed at one focal point position f1, a two-dimensional scanning optical system employed by SLO is disposed at another one focal point position f2, and a two-dimensional scanning optical system employed by OCT is disposed at yet another one focal point position f3.

In a third aspect, the subject's eye is disposed at one focal point position f1, a shared one-dimensional scanning optical system employed by both SLO and OCT and that scans light in a first direction is disposed at another one focal point position f2, a one-dimensional scanning optical system that scans light in a second direction intersecting the first direction (for example, an orthogonal direction) employed by SLO is disposed at yet another one focal point position f3, and a one-dimensional scanning optical system that scans light in a second direction employed in OCT is disposed at an optically equivalent position to the another one focal point position f3.

Note that in each of the aspects above, the subject's eye and a scanning optical system may be disposed at a position optically equivalent to a focal point position instead of a focal point position.

In the exemplary embodiments explained above, a microelectrochemical system (MEMS) mirror, a rotating mirror, a prism, a resonating mirror, or the like may be employed instead of the polygon mirror 44.

In the exemplary embodiments explained above, a MEMS mirror, a rotating mirror, a prism, a polygonal scanner, or a resonating mirror may be employed instead of the V-galvanometer mirror 60 and the H-galvanometer mirror 68.

Although examples have been given in each of the exemplary embodiments above in which a pair of concave mirrors are configured by the slit mirror 66 and the ellipsoid mirror 70, the present invention is not limited thereto. For example, a tilted spherical mirror, a non-spherical mirror, a pair of parabola mirrors, a pair of parabolic mirrors, a lens system, or an optical system employing an appropriate combination of these may be employed instead of the slit mirror 66.

Furthermore, the fixation target light control processing explained in each of the exemplary embodiments above are merely examples. It therefore goes without saying that unnecessary steps may be omitted, new steps may be added, and the processing sequence may be rearranged. Moreover, each item of OCT imaging processing may be implemented by hardware configuration alone, such as an FPGA, an ASIC, or the like, or may be implemented by a combination of a computer employing software configuration and hardware configuration.

Although description has been given above of exemplary embodiments of the present invention with reference to the drawings, the specific configuration of the exemplary embodiments are not limited thereto, and encompass designs and the like within a range not departing from the spirit and scope of the present invention.

All publications, patent applications and technical standards mentioned in the present specification are incorporated by reference in the present specification to the same extent as if each individual publication, patent application, or technical standard was specifically and individually indicated to be incorporated by reference.

The invention claimed is:

1. A method of controlling an ophthalmic device having a first retinal image acquisition module operable to image an imaging region of a retina and an illumination module operable to concurrently illuminate an illumination region of the retina, the imaging region and the illumination region having a predetermined positional relationship to one another, the method comprising:

controlling the first retinal image acquisition module to acquire a reference retinal image by imaging a reference imaging area of the retina;

designating a target in the reference retinal image;

controlling the first retinal image acquisition module to acquire a current retinal image of an initial imaging region within the reference imaging area;

controlling the first retinal image acquisition module to move its imaging region of the retina from the initial imaging region to a destination imaging region using the target and at least a portion of the reference retinal image, and to acquire a retinal image of the destination imaging region, wherein the using includes comparing positions of the current retinal image and target within the reference retinal image, the position of the current retinal image being determined based on a matching of features in the current retinal image and reference retinal image, and wherein moving of the imaging region to the destination imaging region is performed based on a result of the comparing;

controlling the illumination module to illuminate the illumination region of the retina while the imaging region of the first retinal image acquisition module is the destination imaging region;

controlling the first retinal image acquisition module to acquire one or more retinal images while the illumination module is illuminating the illumination region of the retina; and comparing a marker retinal image based on the one or more retinal images with a comparison image based on at least a portion of the reference retinal image to determine a marker that is indicative of the position of the marker retinal image within the comparison image.

2. The method according to claim 1, wherein:

the illumination module comprises a second retinal image acquisition module which is operable to image a respective imaging region of the retina, the first and second retinal image acquisition modules being operable to concurrently image respective imaging regions of the retina which have a predetermined positional relationship to one another;

the second retinal image acquisition module is controlled to acquire a retinal image while the imaging region of the first retinal image acquisition module is the destination imaging region; and the first retinal image acquisition module is controlled to acquire the one or more retinal images while the second retinal image acquisition module is acquiring the retinal image.

3. The method according to claim 1, further comprising storing the marker in association with at least one of:

the comparison image;
the reference image;
at least one of the one or more retinal images;
the marker retinal image; and
a clipped region of the reference retinal image, the clipped region being positioned at the determined position of the marker retinal image within the reference retinal image.

4. The method according to claim 2, further comprising storing the marker in association with at least one of:

the retinal image acquired by the second retinal image acquisition module;
the comparison image;
the reference image;
at least one of the one or more retinal images;
the marker retinal image; and
a clipped region of the reference retinal image, the clipped region being positioned at the determined position of the marker retinal image within the reference retinal image.

5. The method according to claim 1, wherein the using comprises:

(i) determining the position of the current retinal image based on the matching;

(ii) performing the comparing of the positions of the current retinal image and the target within the reference retinal image and, based on the result of the comparing, determining an adjustment to move a current imaging region of the first retinal image acquisition module closer to a target location on the retina corresponding to the target in the reference retinal image;

(iii) using the adjustment to control the first retinal image acquisition module to set the imaging region of the first retinal image acquisition module to another imaging region within the reference retinal image which becomes the current imaging region; and (iv) controlling the first retinal image acquisition module to acquire a current retinal image of the current imaging region set in process (iii), wherein processes (i) to (iv) are performed at least once, and the retinal image of the destination imaging region is the current retinal image acquired in a final performance of process (iv).

6. The method according to claim 5, wherein processes (i) to (iv) are performed more than once, and the adjustment determined in a second and any subsequent performance of process (ii) is based on at least one adjustment determined in at least one prior performance of process (ii).

7. The method according to claim 5, further comprising generating display data for displaying an indication of the adjustment determined in at least one performance of process (ii) on a display.

8. The method according to claim 5, wherein the processes (i) to (iv) are repeated a predetermined number of times or until positions of the current retinal image acquired in process (iv) and the target coincide within a predefined margin of error.

9. The method according to claim 2, further comprising controlling the ophthalmic device to acquire a second retinal image by the second retinal image acquisition module during a repeat image acquisition process, by:

controlling the first retinal image acquisition module to acquire a second reference retinal image by imaging a second reference imaging area of the retina;

designating a target in the second reference retinal image using the marker, the comparison image and the second reference retinal image;

controlling the first retinal image acquisition module to acquire a current retinal image of an initial imaging region within the second reference imaging area;

controlling the first retinal image acquisition module to move its imaging region from the initial imaging region within the second reference imaging area to a destination imaging region within the second reference imaging area using the target in the second reference retinal image and the second reference retinal image, and to acquire a retinal image of the destination imaging region within the second reference imaging region;

controlling the second retinal image acquisition module to acquire, as the second retinal image, an image in the imaging region of the second retinal image acquisition module while the imaging region of the first retinal image acquisition module is the destination imaging region;

controlling the first retinal image acquisition module to acquire one or more further retinal images while the second retinal image acquisition module is acquiring the second retinal image; and comparing a second marker retinal image based on the one or more further retinal images with a second comparison image based on at least a portion of the second reference retinal image to determine a second marker that is indicative of the position of the second marker retinal image within the second comparison image.

10. The method according to claim 9, wherein the first retinal image acquisition module is controlled to move its imaging region from the initial imaging region within the second reference retinal image to the destination imaging region within the second reference retinal image by performing following processes (a) to (d) at least once:
  (a) determining a position of the current retinal image within the second reference retinal image by comparing the current retinal image with the second reference retinal image;
  (b) comparing the position of the current retinal image within the second reference retinal image with a position of the target within the second reference retinal image and, based on the comparison, determining an adjustment to move the current imaging region of the first retinal image acquisition module closer to a target on the retina corresponding to the target in the-second reference retinal image;
  (c) using the adjustment to control the first retinal image acquisition module to set the imaging region of the first retinal image acquisition module to another imaging region within the second reference retinal image which becomes the current imaging region;
  (d) controlling the first retinal image acquisition module to acquire a current retinal image of the current imaging region set in process (c),
wherein the retinal image of the destination imaging region within the second reference imaging area is the retinal image acquired in the final performance of process (d), and wherein the sequence of processes (a) to (d) is repeated a predetermined number of times or until the position within the second reference retinal image of the retinal image acquired in process (d) coincides with the position of the target within the second reference retinal image to within a second predefined margin of error.

11. The method according to claim 10, further comprising storing the second comparison image in association with the second marker.

12. The method according to claim 11, comprising storing the second marker in association with at least one of:
  the second comparison image;
  the second retinal image acquired by the second retinal image acquisition module;
  at least one of the one or more further retinal images;
  the second marker retinal image; and
  a clipped region of the second reference retinal image, the clipped region being positioned at the determined position of the second marker retinal image within the second reference retinal image.

13. The method according to claim 1, further comprising:
  comparing a second marker retinal image based on another one or more retinal images with a second comparison image that is based on at least a portion of the reference retinal image to determine a second marker that is indicative of the position of the second marker retinal image within the second comparison image;
  determining a relative offset between the positions of the first and second marker retinal images in the reference retinal image; and
  performing at least one of storing the determined relative offset and displaying the determined relative offset on a display.

14. The method according to claim 9, further comprising:
  comparing a third marker retinal image based on another one or more retinal images with a third comparison image that is based on at least a portion of the second reference retinal image to determine a third marker that is indicative of the position of the third marker retinal image within the third comparison image;
  determining a relative offset between the positions of the second and third marker retinal images in the second reference retinal image; and
  performing at least one of storing the determined relative offset and displaying the determined relative offset on a display.

15. The method according to claim 2, wherein the first retinal image acquisition module comprises a scanning ophthalmoscope configured to produce scans of the retina, and the second retinal image acquisition module comprises an optical coherence tomography imaging module configured to produce tomographic images of the retina.

16. The method according to claim 15, wherein the scanning ophthalmoscope is arranged to produce, as the reference retinal image, up to a 180 degree scan of the retina, as measured at the center of the eye.

17. The method according to claim 16, wherein the scanning ophthalmoscope is arranged to produce, as the reference retinal image, up to a 120 degree scan of the retina, as measured at the center of the eye.

18. The method according to claim 17, wherein the scanning ophthalmoscope is arranged to produce, as the reference retinal image, up to an 80 degree scan of the retina, as measured at the center of the eye.

19. A non-transitory computer-readable storage medium storing computer program instructions which, when executed by a processor, cause the processor to perform a method of controlling an ophthalmic device having a retinal image acquisition module operable to image an imaging region of a retina and an illumination module operable to concurrently illuminate an illumination region of the retina, the imaging region and the illumination region having a predetermined positional relationship to one another, the method comprising:
  controlling the retinal image acquisition module to acquire a reference retinal image by imaging a reference imaging area of the retina;
  designating a target in the reference retinal image;
  controlling the retinal image acquisition module to acquire a current retinal image of an initial imaging region within the reference imaging area;
  controlling the retinal image acquisition module to move its imaging region of the retina from the initial imaging region to a destination imaging region using the target and at least a portion of the reference retinal image, and to acquire a retinal image of the destination imaging region, wherein the using includes comparing positions of the current retinal image and target within the reference retinal image, the position of the current retinal image being determined based on a matching of features in the current retinal image and reference retinal image, and wherein moving of the imaging region to the destination imaging region is performed based on a result of the comparing;
  controlling the illumination module to illuminate the illumination region of the retina while the imaging region of the retinal image acquisition module is the destination imaging region;

controlling the retinal image acquisition module to acquire one or more retinal images while the illumination module is illuminating the illumination region of the retina; and comparing a marker retinal image based on the one or more retinal images with a comparison image based on at least a portion of the reference retinal image to determine a marker that is indicative of the position of the marker retinal image within the comparison image.

20. A controller for controlling an ophthalmic device having a retinal image acquisition module operable to image an imaging region of a retina and an illumination module operable to concurrently illuminate an illumination region of the retina, the imaging region and the illumination region having a predetermined positional relationship to one another, the controller comprising a processor and a memory storing computer program instructions which, when executed by the processor, cause the processor to perform a method of controlling the ophthalmic device, the method comprising:

controlling the retinal image acquisition module to acquire a reference retinal image by imaging a reference imaging area of the retina;

designating a target in the reference retinal image;

controlling the retinal image acquisition module to acquire a current retinal image of an initial imaging region within the reference imaging area;

controlling the retinal image acquisition module to move its imaging region of the retina from the initial imaging region to a destination imaging region using the target and at least a portion of the reference retinal image, and to acquire a retinal image of the destination imaging region, wherein the using includes comparing positions of the current retinal image and target within the reference retinal image, the position of the current retinal image being determined based on a matching of features in the current retinal image and reference retinal image, and wherein moving of the imaging region to the destination imaging region is performed based on a result of the comparing;

controlling the illumination module to illuminate the illumination region of the retina while the imaging region of the retinal image acquisition module is the destination imaging region;

controlling the retinal image acquisition module to acquire one or more retinal images while the illumination module is illuminating the illumination region of the retina; and comparing a marker retinal image based on the one or more retinal images with a comparison image based on at least a portion of the reference retinal image to determine a marker that is indicative of the position of the marker retinal image within the comparison image.

21. An ophthalmic device comprising:

a retinal image acquisition module arranged to acquire a retinal image of an imaging area of the retina of an eye;

an illumination module operable to concurrently illuminate an illumination region of the retina, the imaging region and the illumination region having a predetermined positional relationship to one another; and a controller arranged to control the retinal image acquisition module and the illumination module, the controller comprising a processor and a memory storing computer program instructions which, when executed by the processor, cause the processor to perform a method of controlling the ophthalmic device, the method comprising:

controlling the retinal image acquisition module to acquire a reference retinal image by imaging a reference imaging area of the retina;

designating a target in the reference retinal image;

controlling the retinal image acquisition module to acquire a current retinal image of an initial imaging region within the reference imaging area;

controlling the retinal image acquisition module to move its imaging region of the retina from the initial imaging region to a destination imaging region using the target and at least a portion of the reference retinal image, and to acquire a retinal image of the destination imaging region, wherein the using includes comparing positions of the current retinal image and target within the reference retinal image, the position of the current retinal image being determined based on a matching of features in the current retinal image and reference retinal image, and wherein moving of the imaging region to the destination imaging region is performed based on a result of the comparing;

controlling the illumination module to illuminate the illumination region of the retina while the imaging region of the retinal image acquisition module is the destination imaging region;

controlling the retinal image acquisition module to acquire one or more retinal images while the illumination module is illuminating the illumination region of the retina; and comparing a marker retinal image based on the one or more retinal images with a comparison image based on at least a portion of the reference retinal image to determine a marker that is indicative of the position of the marker retinal image within the comparison image.

* * * * *